US012622654B2

(12) United States Patent
Shimizukawa et al.

(10) Patent No.: US 12,622,654 B2
(45) Date of Patent: May 12, 2026

(54) COMPUTED TOMOGRAPHY APPARATUS

(71) Applicant: FUJIFILM CORPORATION, Tokyo (JP)

(72) Inventors: Sho Shimizukawa, Kanagawa (JP); Tatsuya Taneichi, Kanagawa (JP); Takashi Tajima, Kanagawa (JP); Naoyuki Nishino, Kanagawa (JP); Hisatsugu Horiuchi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 359 days.

(21) Appl. No.: 18/448,980

(22) Filed: Aug. 14, 2023

(65) Prior Publication Data

US 2024/0065646 A1    Feb. 29, 2024

(30) Foreign Application Priority Data

Aug. 23, 2022    (JP) ................................. 2022-132603

(51) Int. Cl.
*A61B 6/00*        (2024.01)
*A61B 6/03*        (2006.01)
*A61B 6/40*        (2024.01)

(52) U.S. Cl.
CPC ............ *A61B 6/035* (2013.01); *A61B 6/4014* (2013.01); *A61B 6/4085* (2013.01)

(58) Field of Classification Search
CPC ............................... A61B 6/032; A61B 6/4014
See application file for complete search history.

(56) References Cited

U.S. PATENT DOCUMENTS

| | | |
|---|---|---|
| 2008/0260101 A1 | 10/2008 | Oreper |
| 2012/0121062 A1 | 5/2012 | Sowards-Emmerd et al. |

(Continued)

FOREIGN PATENT DOCUMENTS

| | | |
|---|---|---|
| JP | 2006-122483 A | 5/2006 |
| JP | 2006-346011 A | 12/2006 |
| WO | 2012/046813 A1 | 4/2012 |

OTHER PUBLICATIONS

English language translation of the following: Office action dated Mar. 31, 2026 from the JPO in a Japanese patent application No. 2022-132603 corresponding to the instant patent application. This office action translation is submitted now in order to supplement the understanding of the cited references which are being disclosed in the isntant information Disclosure Statement.

*Primary Examiner* — Dani Fox
(74) *Attorney, Agent, or Firm* — SOLARIS Intellectual Property Group, PLLC

(57) ABSTRACT

A radiation source includes a radiation tube having a cathode which is a cold cathode. An imaging control unit directs the radiation source to intermittently and alternately emit the first radiation having a first energy distribution and the second radiation having a second energy distribution different from the first energy distribution whenever a rotation mechanism rotates the radiation source and a radiation detector by a preset angle. The imaging control unit directs the radiation detector to output a first projection image based on the first radiation and a second projection image based on the second radiation which are obtained by the intermittent emission of the first radiation and the second radiation. An image processing unit generates a tomographic image on the basis of the first projection image and the second projection image.

8 Claims, 34 Drawing Sheets

(56)         References Cited

U.S. PATENT DOCUMENTS

| | | |
|---|---|---|
| 2013/0208960 A1 | 8/2013 | Reisman |
| 2013/0308746 A1 | 11/2013 | Ueki |
| 2015/0305697 A1* | 10/2015 | Tamura ................. A61B 6/035 |
| | | 378/5 |
| 2019/0239833 A1 | 8/2019 | Ikhlef |
| 2022/0079534 A1* | 3/2022 | Morf ................... A61N 5/1049 |

* cited by examiner

Figure 17:
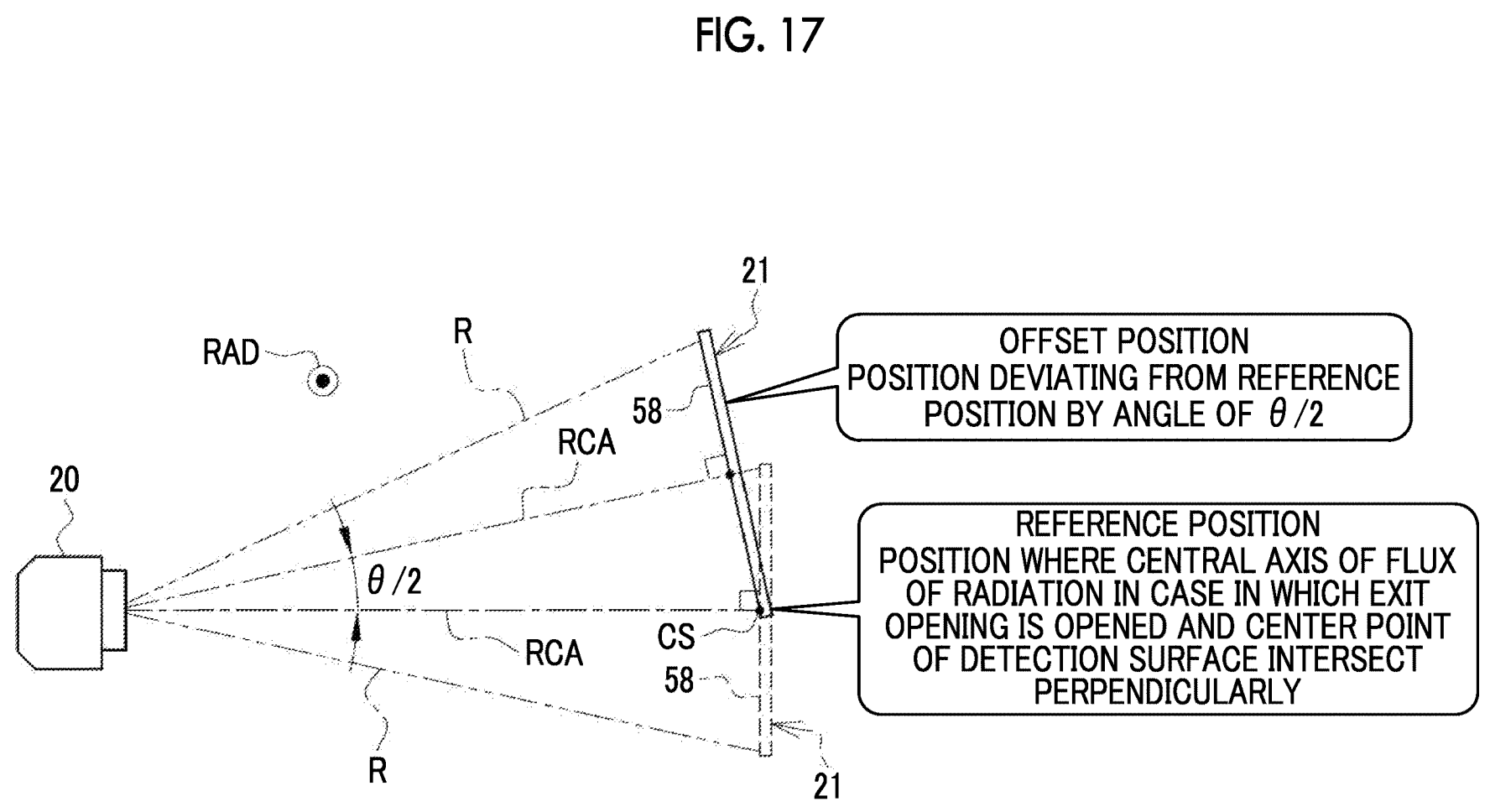

OFFSET POSITION
POSITION DEVIATING FROM REFERENCE
POSITION BY ANGLE OF $\theta/2$ REFERENCE POSITION
POSITION WHERE CENTRAL AXIS OF FLUX
OF RADIATION IN CASE IN WHICH EXIT
OPENING IS OPENED AND CENTER POINT
OF DETECTION SURFACE INTERSECT
PERPENDICULARLY

FIG. 28

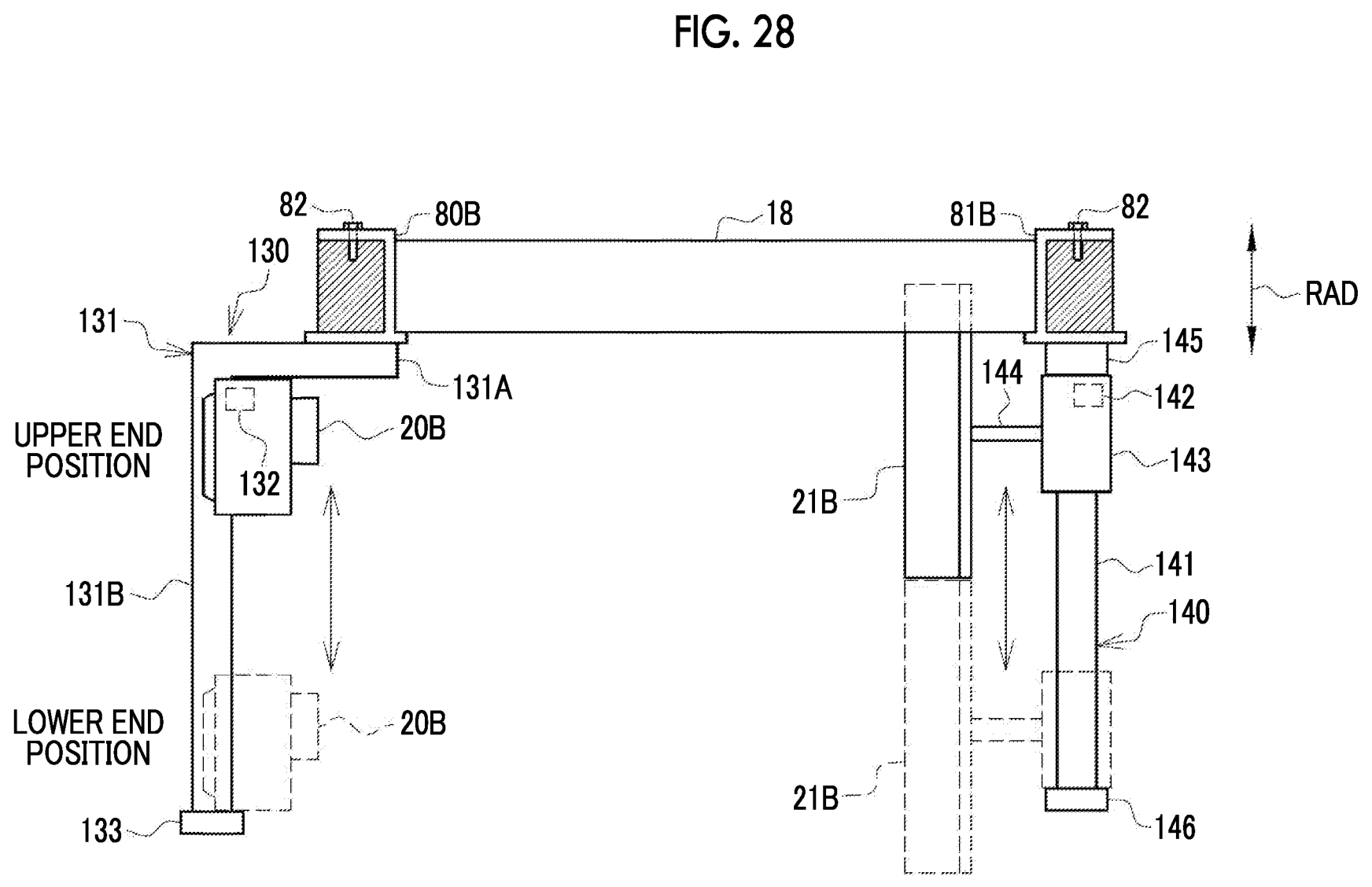

RAD 82
145
142
143
141
140
146

81B
144

21B

21B

18

80B

131A

20B 82
130
132

131

UPPER END
POSITION

131B

20B

LOWER END
POSITION

Figure 32:
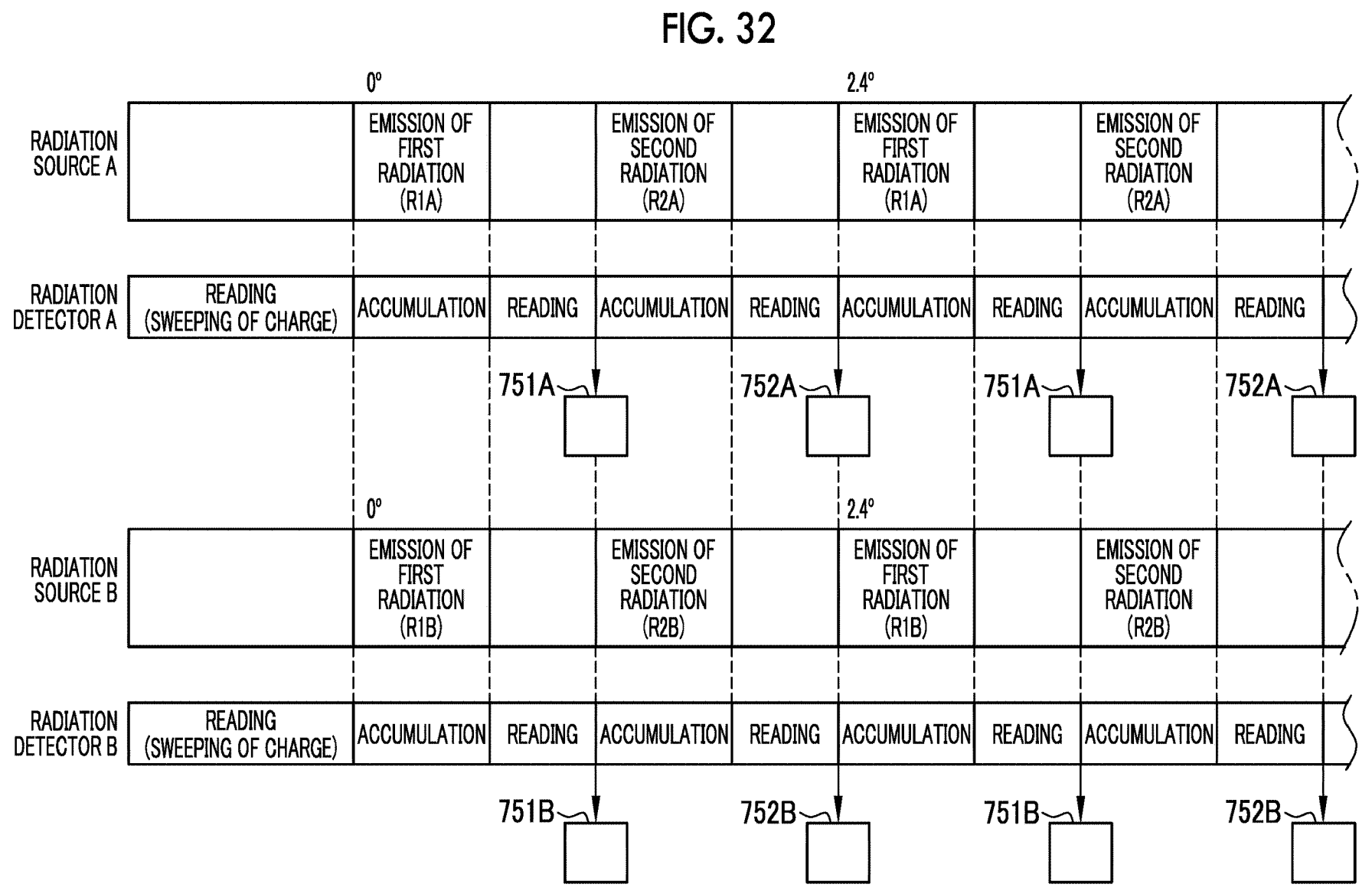

| | | | | | | | |
|---|---|---|---|---|---|---|---|
| | 0° | | 2.4° | | | | |
| RADIATION SOURCE A | EMISSION OF FIRST RADIATION (R1A) | EMISSION OF SECOND RADIATION (R2A) | EMISSION OF FIRST RADIATION (R1A) | EMISSION OF SECOND RADIATION (R2A) | | | |
| RADIATION DETECTOR A | READING (SWEEPING OF CHARGE) | ACCUMULATION | READING | ACCUMULATION | READING | ACCUMULATION | READING |
| | | 751A | 752A | 751A | 752A | | |
| | 0° | | 2.4° | | | | |
| RADIATION SOURCE B | EMISSION OF FIRST RADIATION (R1B) | EMISSION OF SECOND RADIATION (R2B) | EMISSION OF FIRST RADIATION (R1B) | EMISSION OF SECOND RADIATION (R2B) | | | |
| RADIATION DETECTOR B | READING (SWEEPING OF CHARGE) | ACCUMULATION | READING | ACCUMULATION | READING | ACCUMULATION | READING |
| | | 751B | 752B | 751B | 752B | | |

FIG. 36

COMPUTED TOMOGRAPHY APPARATUS

CROSS-REFERENCE TO RELATED APPLICATIONS

The present application claims priority under 35 U.S.C. § 119 to Japanese Patent Application No. 2022-132603, filed on Aug. 23, 2022. The above application is hereby expressly incorporated by reference, in its entirety, into the present application.

BACKGROUND

1. Technical Field

The technology of the present disclosure relates to a computed tomography apparatus.

2. Description of the Related Art

JP2006-346011A discloses a computed tomography apparatus (hereinafter, referred to as a CT apparatus) that images a subject in a decubitus posture or a sitting posture and comprises two imaging units each of which is composed of a radiation source that emits radiation to the subject and a radiation detector that detects the radiation transmitted through the subject and outputs a projection image. The two imaging units are disposed at an interval of 90° in a gantry that is rotated around a body axis of the subject. The radiation source emits a cone beam, and the radiation detector has a configuration in which a plurality of pixels are arranged in a two-dimensional matrix.

In JP2006-346011A, one of the two imaging units emits first radiation having a first energy distribution, and the other emits second radiation having a second energy distribution different from the first energy distribution. The two imaging units irradiate the subject with the first radiation and the second radiation at the same time whenever the gantry is rotated by a preset angle. Therefore, a first projection image and a second projection image of the subject irradiated with the radiation components having different energy levels are obtained.

In JP2006-346011A, an energy subtraction (hereinafter, referred to as ES) process is performed on the first projection image and the second projection image to generate an ES image in which a specific biological tissue has been highlighted. Specifically, the ES image is generated from the first projection image and the second projection image obtained at the same rotation position. Then, a reconstruction process is performed on the ES images at each rotation position to generate a tomographic image. The specific biological tissue is a bone tissue, such as a rib or a backbone, or a soft tissue, such as a lung or a stomach.

SUMMARY

In the CT apparatus described in JP2006-346011A, since the two imaging units are disposed at an interval of 90°, the imaging angles of the subject in the first projection image and the second projection images obtained at the same time are different. Therefore, it is not possible to generate the ES image from the first projection image and the second projection image obtained at the same time. Therefore, it is considered that the ES image is generated from the first projection image and the second projection image obtained at the same rotation position, for example, the first projection image obtained in a case in which one of the imaging units is at a position of 0° and the second projection image obtained in a case in which the other imaging unit is rotated by 90° and reaches the position of 0°. However, in this method, a time lag occurs between the acquisition time of the first projection image and the acquisition time of the second projection image, and imaging is greatly affected by the body movement of the subject.

The inventors have conceived a CT apparatus for obtaining a tomographic image of a subject in a standing posture or a sitting posture. Further, in order to solve the above-described problems of the CT apparatus described in JP2006-346011A, a configuration is considered in which one radiation source continuously emits the first radiation and the second radiation to obtain the first and second projection images, in which the imaging angles of the subject are almost the same, substantially at the same time at each rotation position.

However, in this case, it is necessary to speed up the switching between the emission of the first radiation and the emission of the second radiation in order to secure the synchronism of the first projection image and the second projection image. In addition, in order to generate a tomographic image having reasonable quality, it is better to obtain a larger number of first and second projection images at a preset rotation speed. For that purpose, it is necessary to speed up the switching between the emission of the first radiation and the emission of the second radiation. Further, a subject in the standing posture or the sitting posture is more unstable and is more likely to make a body movement than a subject in a decubitus posture. From this point of view, it is also necessary to speed up the switching between the emission of the first radiation and the emission of the second radiation.

One embodiment according to the technology of the present disclosure provides a computed tomography apparatus that can speed up switching between the emission of first radiation and the emission of second radiation.

According to the present disclosure, there is provided a computed tomography apparatus comprising: a radiation source that emits radiation having a pyramid shape to a subject positioned in either a standing posture or a sitting posture and that includes a radiation tube having a cold cathode; a radiation detector in which a plurality of pixels detecting the radiation transmitted through the subject are two-dimensionally arranged and which outputs a projection image of the subject; a rotation mechanism that rotates the radiation source and the radiation detector around a body axis of the subject; and a processor that controls operations of the radiation source, the radiation detector, and the rotation mechanism. The processor directs the radiation source to continuously emit first radiation having a first energy distribution and second radiation having a second energy distribution different from the first energy distribution whenever the rotation mechanism rotates the radiation source and the radiation detector by a preset angle, directs the radiation detector to output a first projection image based on the first radiation and a second projection image based on the second radiation which are obtained by the continuous emission of the first radiation and the second radiation, and generates a tomographic image on the basis of the first projection image and the second projection image.

Preferably, the cold cathode is a field emission type having an electron emission source that emits an electron beam using a field emission phenomenon.

Preferably, the computed tomography apparatus further comprises a plurality of imaging units each of which is composed of a set of the radiation source and the radiation detector and which have different phases in a rotation direction.

Preferably, the computed tomography apparatus further comprises a displacement mechanism that changes an interval between the plurality of imaging units in a rotation axis direction.

Preferably, the processor sets the interval such that an overlapping imaging range occurs between the projection images obtained by the imaging units adjacent to each other in a case in which an imaging range that exceeds a width of a detection surface for the radiation in the radiation detector is imaged, performs a reconstruction process on the projection images obtained from each of the plurality of imaging units to generate a plurality of the tomographic images for each of the plurality of imaging units, and registers the plurality of tomographic images on the basis of the overlapping imaging range to combine the plurality of tomographic images.

Preferably, the radiation detector has a configuration in which a plurality of detection units for the radiation are arranged along a direction orthogonal to a rotation axis direction of the radiation source and the radiation detector.

Preferably, the radiation detector is disposed at an offset position that is separated from a reference position facing the radiation source by a preset angle as viewed from a rotation axis direction of the radiation source and the radiation detector.

Preferably, the radiation source and the radiation detector are held in a frame, and the subject is positioned in the frame. Preferably, the radiation source is disposed outside the frame, and the radiation detector is disposed inside the frame as viewed from a rotation axis direction of the radiation source and the radiation detector.

Preferably, the processor uses a compression sensing method in a case in which a reconstruction process is performed on the projection images to generate the tomographic image.

Preferably, a width of a detection surface for the radiation in the radiation detector is equal to or greater than 300 mm.

According to the technology of the present disclosure, it is possible to provide a computed tomography apparatus that can speed up switching between the emission of first radiation and the emission of second radiation.

BRIEF DESCRIPTION OF THE DRAWINGS

Exemplary embodiments according to the technique of the present disclosure will be described in detail based on the following figures, wherein:

FIG. 16 is a diagram illustrating the positions where the radiation source and the radiation detector are disposed;

FIG. 17 is a diagram illustrating a reference position and an offset position of the radiation detector;

FIG. 28 is a diagram illustrating a radiation source elevating mechanism and a detector elevating mechanism;

FIG. 30 is a diagram illustrating a flux of radiation in a case in which both of the two imaging units are located at the upper end position;

FIG. 32 is a timing chart illustrating the time when the radiation source emits the radiation and the time when the radiation detector reads the projection image in the second embodiment;

FIG. 36 is a diagram illustrating a radiation detector having a configuration in which a plurality of radiation detection units are arranged.

DETAILED DESCRIPTION

Figure 1:
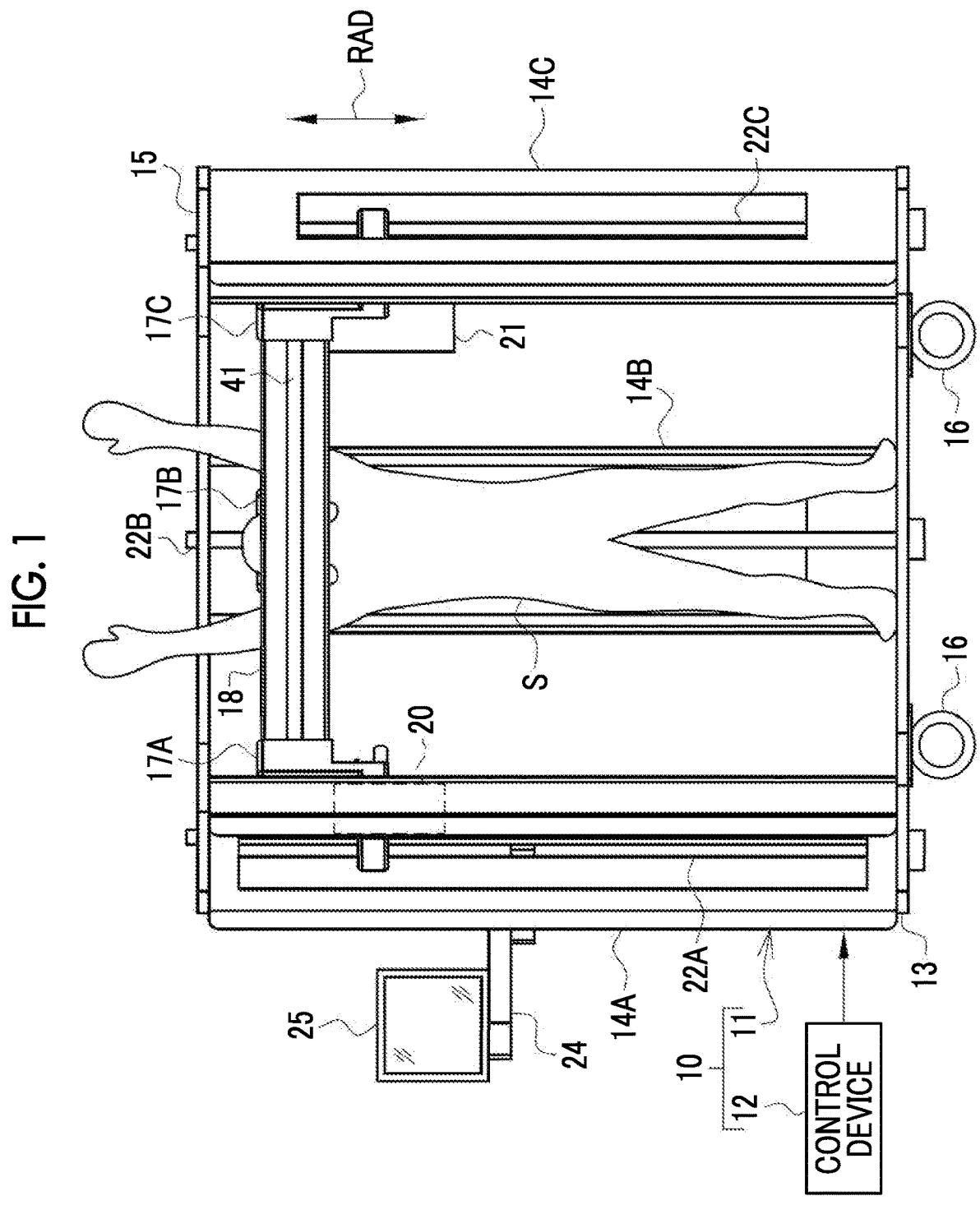
FIG. 1 is a front view illustrating a CT apparatus.

For example, as illustrated in FIG. 1, a CT apparatus 10 is an apparatus for obtaining a tomographic image of a subject S and is composed of an apparatus main body 11 and a control device 12. The apparatus main body 11 is installed, for example, in an imaging room of a medical facility. The control device 12 is installed, for example, in a control room next to the imaging room. The control device 12 is a desktop personal computer, a notebook personal computer, or a tablet terminal. The control device 12 is operated by an operator of the CT apparatus 10 such as a medical radiologist.

Figure 2:
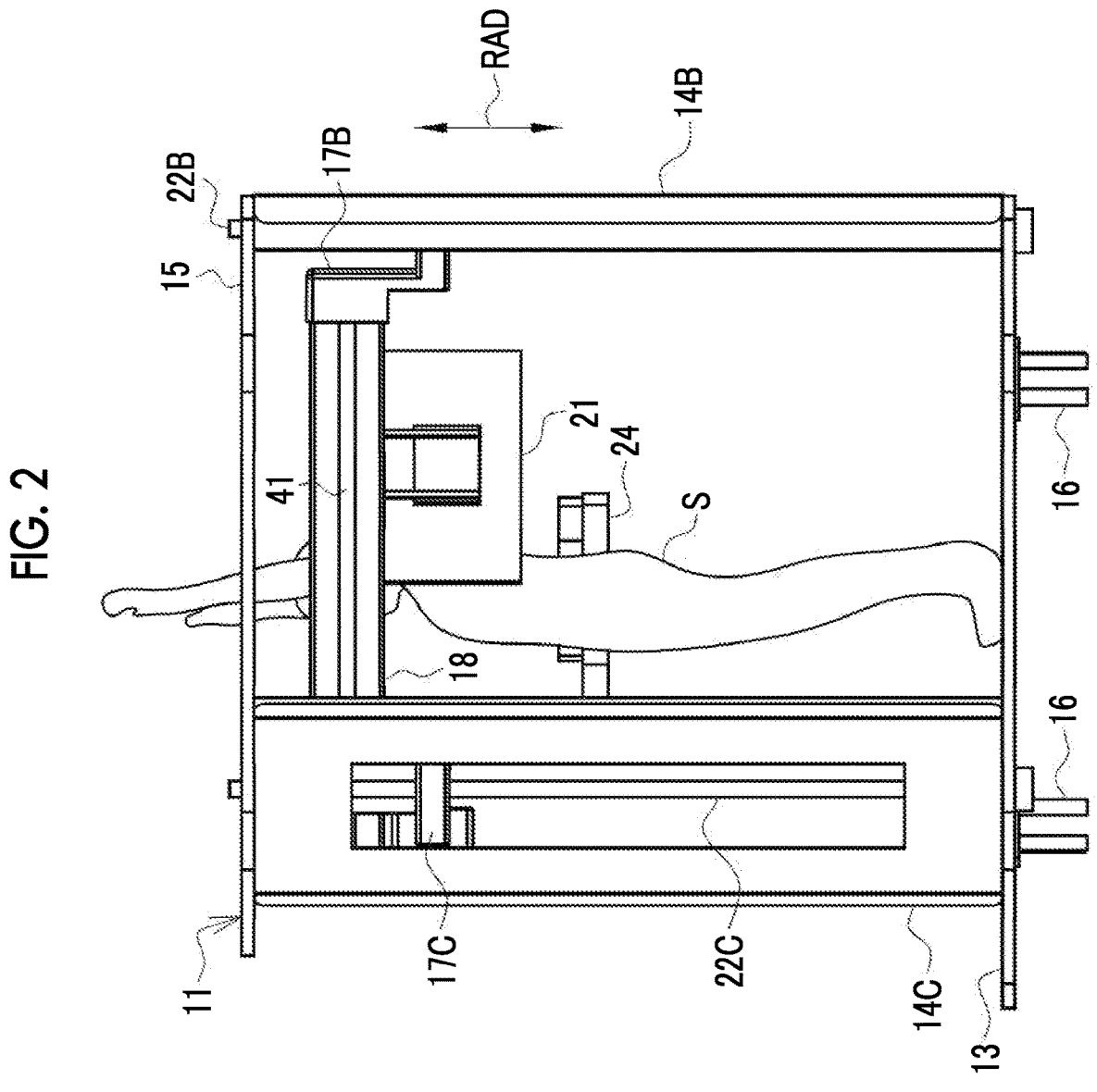
FIG. 2 is a side view illustrating the CT apparatus.

For example, as illustrated in FIG. 2, the apparatus main body 11 comprises a stage 13, three columns 14A, 14B, and 14C, and a top plate 15. The stage 13 is, for example, an octagonal flat plate (see FIG. 6). Casters 16 for transportation are attached to four corners of a rear surface of the stage 13. The caster 16 comprises a rotation lock mechanism (not illustrated). After the apparatus main body 11 is installed at an installation position, the rotation lock mechanism can be operated to lock the rotation of the caster 16. Alternatively, the caster 16 can be removed from the stage 13. The caster 16 can be removed after the apparatus main body 11 is installed at the installation position.

The outer shape of the columns 14A to 14C is a rectangular plate shape, and the columns 14A to 14C are vertically provided at four corners of the surface of the stage 13. The columns 14A and 14C are disposed on the front left and right sides of the apparatus main body 11 (the front left and right sides of the subject S). The column 14B is disposed at the center of the rear side of the apparatus main body 11 (behind the subject S). The top plate 15 is attached to the upper end portions of the columns 14A to 14C. The top plate 15 is, for example, an octagonal flat plate having an outer shape that follows the stage 13 (see FIG. 6). The top plate 15 has a C-shape in which a central portion is hollowed out in a circular shape and a portion corresponding to the front side of the apparatus main body 11 between the columns 14A and 14C is cut out. Further, in the following description, the columns 14A to 14C are collectively referred to as columns 14 in a case in which they do not need to be distinguished from each other.

A connection member 17A is connected to the column 14A, a connection member 17B is connected to the column 14B, and a connection member 17C is connected to the column 14C. A frame 18 is connected to the connection members 17A to 17C. That is, the columns 14A to 14C and the frame 18 are connected to each other through the connection members 17A to 17C. Furthermore, in the following description, the connection members 17A to 17C are collectively referred to as connection members 17 in a case in which they do not need to be distinguished from each other.

The frame 18 has an annular shape. The subject S is positioned at a center C (see FIG. 6) of the annular frame 18.

FIGS. 1 and 2 illustrate an aspect in which the subject S in a standing posture with both hands raised above the head is positioned.

The column 14 is provided with a guide rail (not illustrated) to which the connection member 17 is fitted. The connection member 17 and thus the frame 18 can be raised and lowered in the vertical direction along the guide rail. That is, the columns 14 hold the frame 18 to be raised and lowered in the vertical direction. In addition, the frame 18 can be rotated around a body axis of the subject S, using an axis passing through the center C in the vertical direction as a rotation axis RTA (see FIG. 3). That is, the columns 14A to 14C hold the frame 18 to be rotatable around the body axis of the subject S. Hereinafter, the center C may be referred to as a rotation center C. An arrow represented by letters RAD indicates a rotation axis direction of the frame 18. The rotation axis direction RAD is parallel to the vertical direction. Here, the body axis is an axis extending from the top of the head to a caudal portion (anus) of the subject S. In a case in which the subject S is in the standing posture or a sitting posture (see FIG. 4), the body axis is parallel to the vertical direction and the rotation axis direction RAD. The term "parallel" means parallel including an error which is generally allowed in the technical field to which the technology of the present disclosure belongs and is not contrary to the gist of the technology of the present disclosure, in addition to perfectly parallel. Further, the columns 14 may be expanded and contracted to change a height position of the frame 18.

Figure 3:
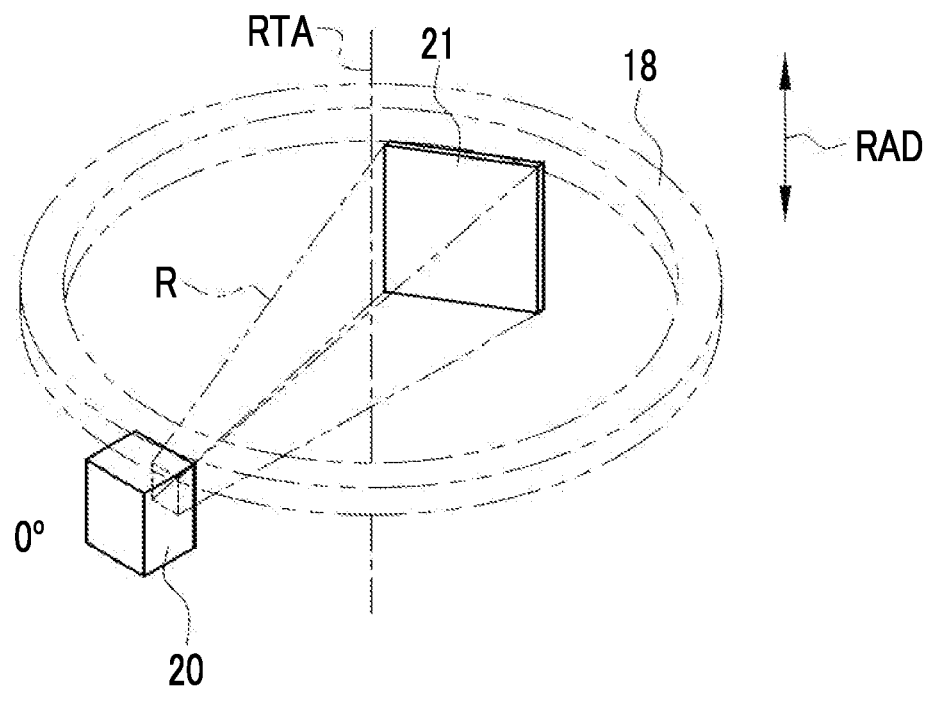
FIG. 3 is a diagram illustrating positions where a radiation source and a radiation detector are disposed.

As illustrated in FIG. 3, a radiation source 20 that irradiates the subject S with radiation R (see FIG. 7), such as X-rays or γ-rays, and a radiation detector 21 that detects the radiation R transmitted through the subject S are attached to the frame 18. The radiation source 20 has a box shape, and the radiation detector 21 has a rectangular plate shape.

The column 14A is provided with a screw shaft 22A, the column 14B is provided with a screw shaft 22B, and the column 14C is provided with a screw shaft 22C. The screw shafts 22A to 22C have a height from the stage 13 to the top plate 15. The screw shafts 22A to 22C are rotated to raise and lower the connection members 17A to 17C and thus the frame 18 in the rotation axis direction RAD. In addition, in the following description, the screw shafts 22A to 22C are collectively referred to as screw shafts 22 in a case in which they do not need to be distinguished from each other.

A touch panel display 25 is attached to the column 14A through a movable arm 24. The touch panel display 25 is operated by the operator. In addition, the touch panel display 25 displays various types of information to the operator.

Figure 4:
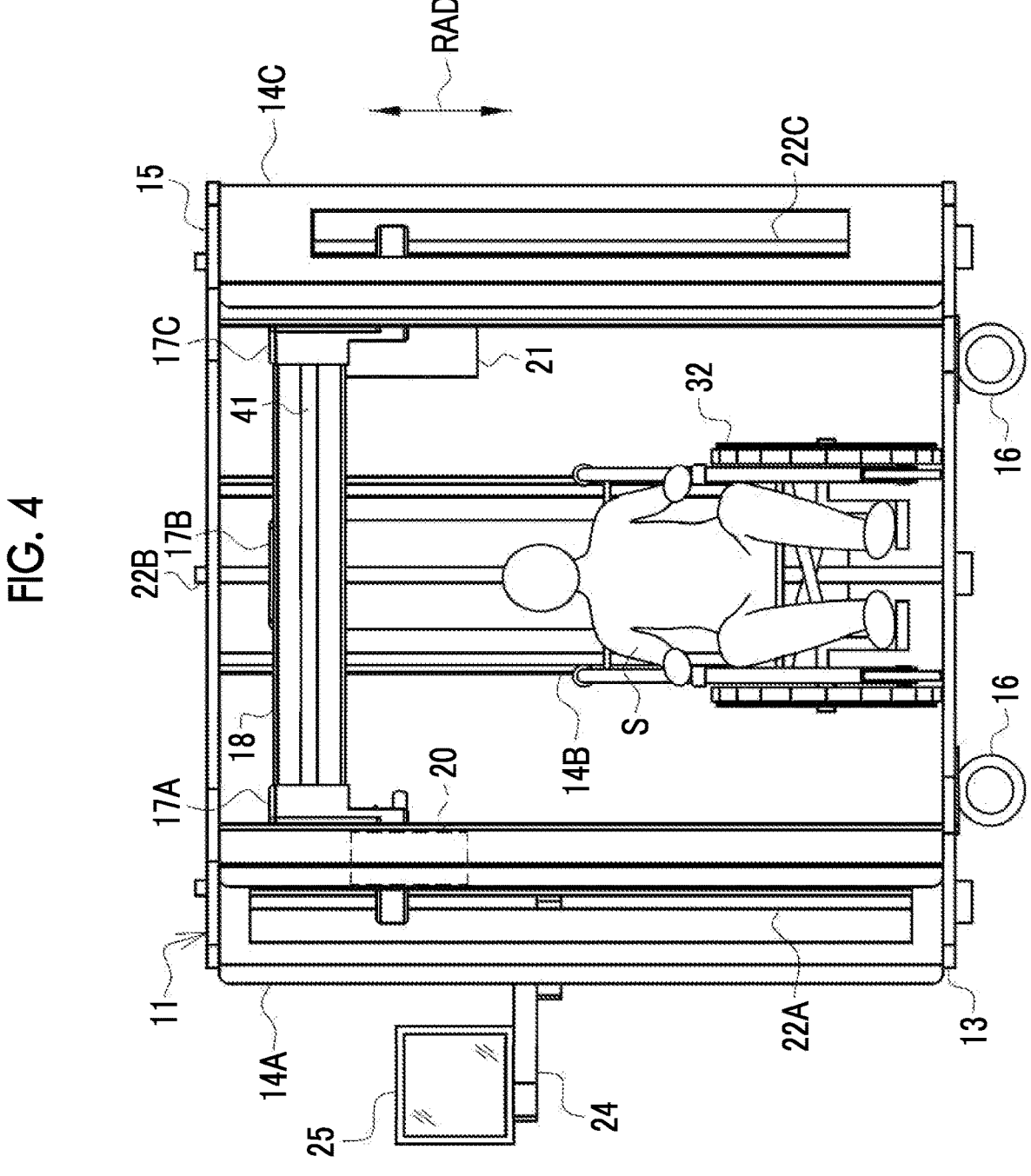
FIG. 4 is a front view of the CT apparatus illustrating a state in which a subject is positioned in a sitting posture on a wheelchair.

FIGS. 1 and 2 illustrate an example in which the subject S is positioned in the frame 18 in the standing posture with both hands raised above the head. However, the present disclosure is not limited thereto. For example, as illustrated in FIG. 4, the CT apparatus 10 can image the subject S who is positioned in the frame 18 in the sitting posture on a wheelchair 32. In addition, either the subject S in the standing posture or the subject S in the sitting posture on the wheelchair 32 is positioned such that the front side faces the columns 14A and 14C and the back side faces the support column 14B.

Figure 5:
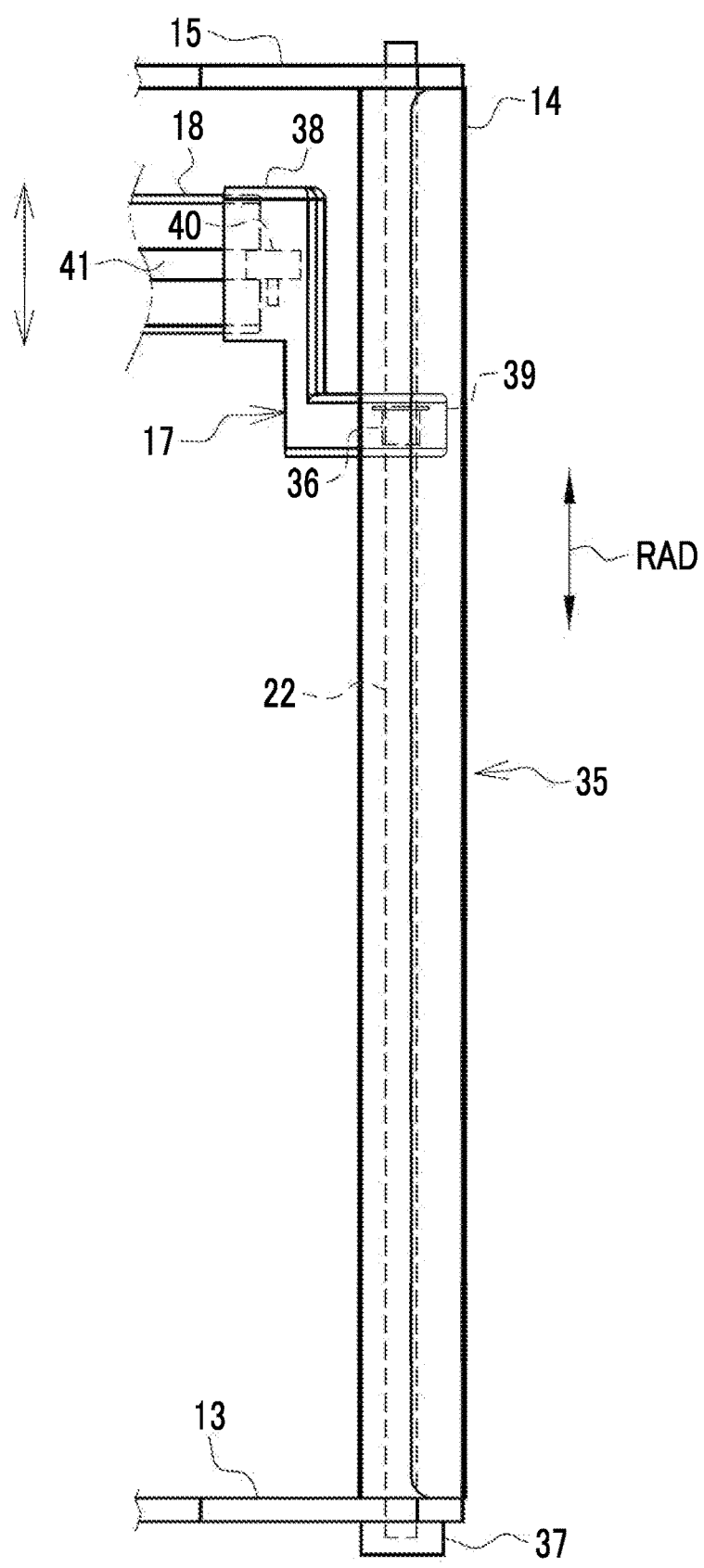
FIG. 5 is a diagram illustrating a frame elevating mechanism.

For example, as illustrated in FIG. 5, a frame elevating mechanism 35 that raises and lowers the connection member 17 and thus the frame 18 in the rotation axis direction RAD is a ball screw mechanism which is composed of the screw shaft 22, a nut 36 that has a ball provided therein and is engaged with the screw shaft 22, a frame elevating motor 37 that rotates the screw shaft 22, and the like. The frame elevating motor 37 is attached to the rear surface of the stage 13. The height position of the frame 18 is determined from the rotation direction and rotation speed of the frame elevating motor 37.

The connection member 17 has a first connection portion 38 that is connected to the frame 18 and a second connection portion 39 that is connected to the column 14. The first connection portion 38 protrudes toward the frame 18, and the second connection portion 39 protrudes toward the column 14. The connection member 17 has a Z-shape as a whole. A bearing 40 is provided in the first connection portion 38. The bearing 40 is fitted to a guide groove 41 (see also FIG. 1 and the like) that is formed over the entire circumference of the frame 18. The bearing 40 rolls as the frame 18 is rotated. The nut 36 is provided in the second connection portion 39.

Figure 6:
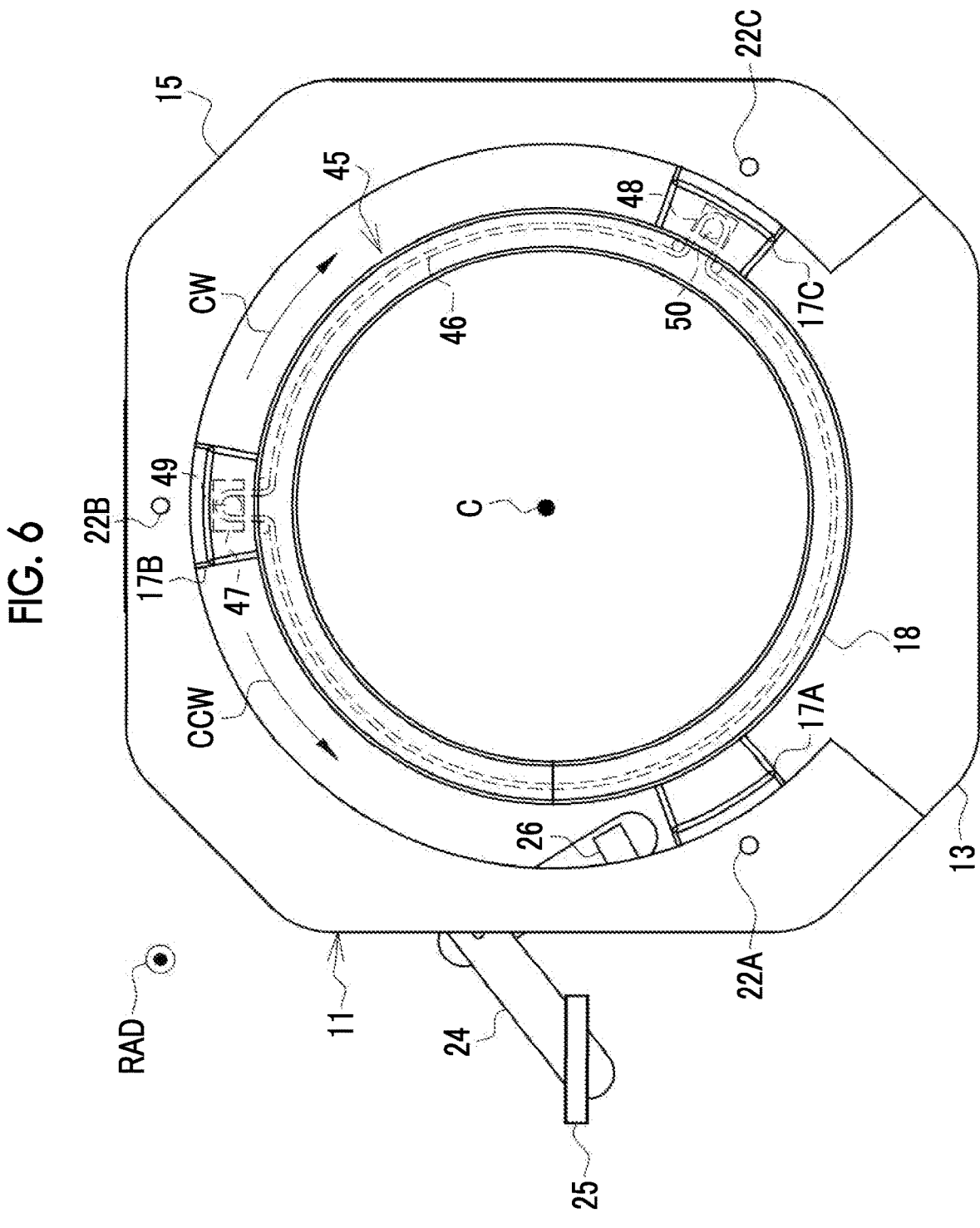
FIG. 6 is a diagram illustrating a rotation mechanism.

For example, as illustrated in FIG. 6, a rotation mechanism 45 that rotates the frame 18 and thus the radiation source 20 and the radiation detector 21 around the body axis of the subject S is composed of a rotation belt 46 that is wound around the entire circumference of the frame 18, a rotary motor 47, a potentiometer 48, and the like. The rotary motor 47 is provided in the connection member 17B and is connected to a portion of the rotation belt 46 drawn out from the frame 18 through a pulley 49. The rotary motor 47 is driven to rotate the frame 18 and thus the radiation source 20 and the radiation detector 21 in a clockwise (right-hand rotation) direction CW and a counterclockwise (left-hand rotation) direction CCW. The rotation speed of the radiation source 20 and the radiation detector 21 is, for example, 36°/second (sec). In this case, the time required for one rotation (360° rotation) of the radiation source 20 and the radiation detector 21 is 10 sec. The clockwise direction CW and the counterclockwise direction CCW are examples of a "rotation direction" according to the technology of the present disclosure.

The potentiometer 48 is provided in the connection member 17C and is connected to a portion of the rotation belt 46 drawn out from the frame 18 through the pulley 50. The potentiometer 48 has a variable resistor whose resistance value is changed depending on the rotation position of the frame 18 and outputs a voltage signal corresponding to the rotation position of the frame 18. The rotation position of the frame 18 is determined by the voltage signal from the potentiometer 48. In addition, in FIG. 6, the radiation source 20 and the radiation detector 21 are not illustrated in order to avoid complication.

Figure 7:
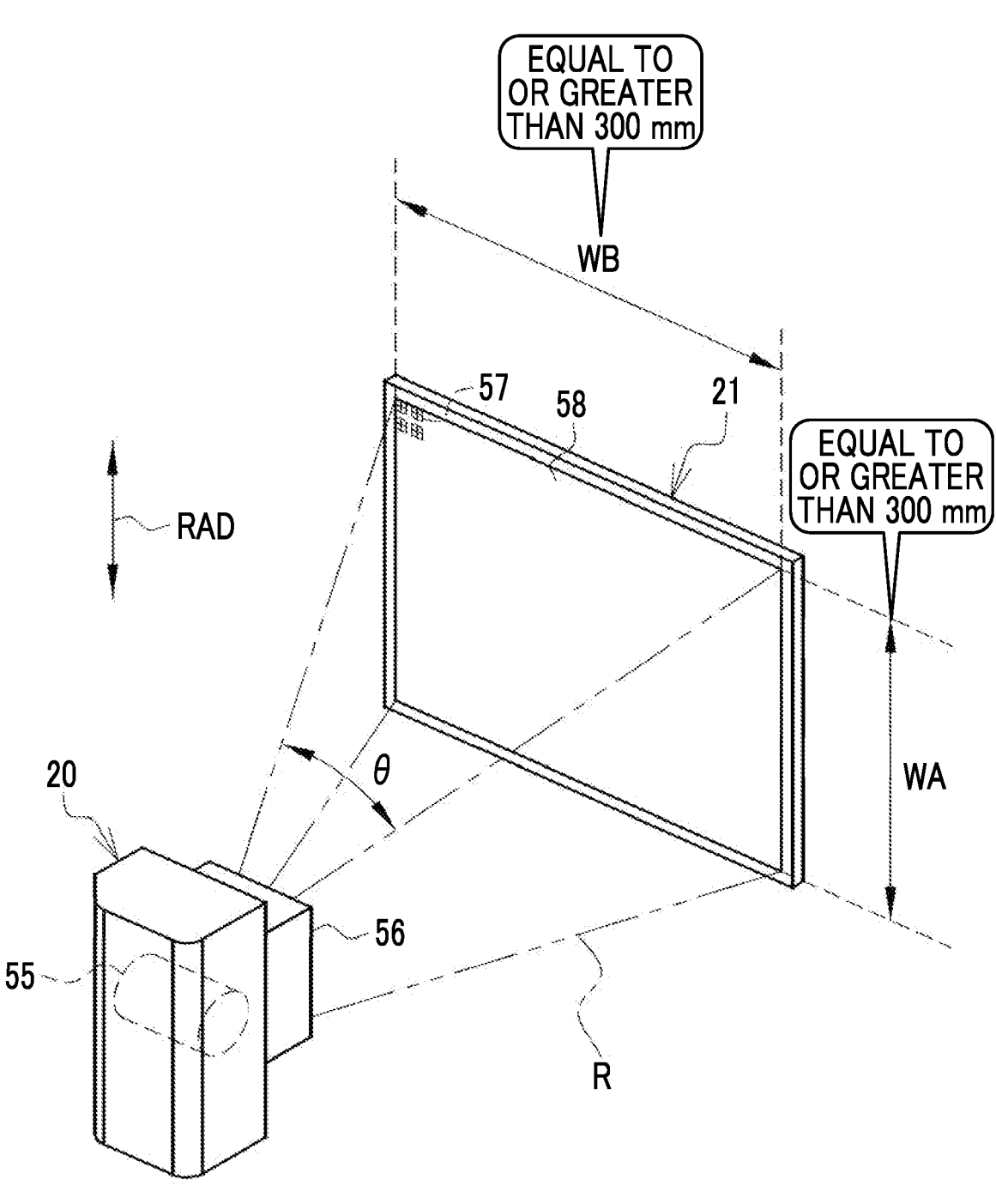
FIG. 7 is a perspective view illustrating a radiation source, a radiation detector, and radiation.

For example, as illustrated in FIG. 7, the radiation source 20 includes a radiation tube 55. The radiation tube 55 emits the radiation R. In addition, the radiation source 20 is also provided with an irradiation field lamp that emits, for example, orange visible light indicating an irradiation field of the radiation R, which is not illustrated.

The radiation source 20 has an irradiation field limiter 56. The irradiation field limiter 56 is also called a collimator and defines the irradiation field of the radiation R to the radiation detector 21. An incident opening through which the radiation R from the radiation tube 55 is incident and an exit opening through which the radiation R exits are formed in the irradiation field limiter 56. For example, four shielding plates are provided in the vicinity of the exit opening. The shielding plate is made of a material that shields the radiation R, for example, lead. The shielding plates are disposed on each side of a quadrangle, in other words, are assembled in a checkered pattern and form a quadrangular irradiation opening through which the radiation R is transmitted. The irradiation field limiter 56 changes the position of each shielding plate to change the size of the irradiation opening, thereby changing the irradiation field of the radiation R to the radiation detector 21. The radiation R having a quadrangular pyramid shape is emitted from the radiation source 20 by the operation of the irradiation field limiter 56. An emission angle θ of the radiation R as viewed from the rotation axis direction RAD is, for example, 10° to 30°. The emission angle θ is also called a cone angle.

The radiation detector 21 is composed of, for example, a scintillator that converts the radiation R into visible light, a thin film transistor (TFT) substrate having a detection surface 58 in which a plurality of pixels 57 that accumulate charge corresponding to the visible light to detect the radiation R are arranged in a two-dimensional matrix, a signal processing circuit that outputs a voltage signal corresponding to the charge as a projection image, and a housing that accommodates these components. Letters WA indicate the width of the detection surface 58 in the rotation axis direction RAD. In addition, letters WB indicate the width of the detection surface 58 in a direction orthogonal to the rotation axis direction RAD. Both the widths WA and WB are equal to or greater than 300 mm. For example, the widths WA and WB are 430 mm (17 inches). A source-to-image distance (SID) which is a distance from a focus F of the radiation R (a point at which the radiation R is emitted in the radiation tube 55 (see FIG. 8)) to the detection surface 58 is, for example, 1200 mm. The width WA is an example of a "width of a detection surface" according to the technology of the present disclosure. In addition, the radiation detector 21 may be a type that directly detects the radiation R instead of the visible light converted from the radiation R.

Figure 8:
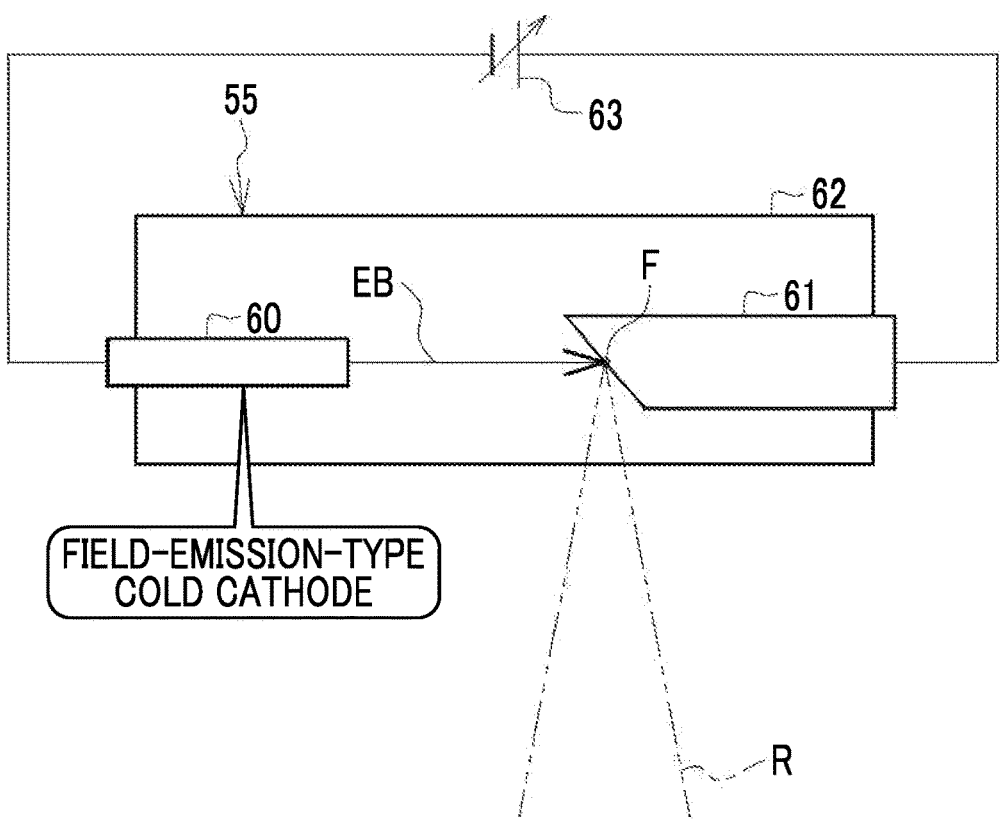
FIG. 8 is a diagram illustrating a radiation tube.

For example, as illustrated in FIG. 8, the radiation tube 55 includes a cathode 60 and an anode 61. The cathode 60 emits electrons. The electrons collide with the anode 61, and the anode 61 emits the radiation R. The cathode 60 and the anode 61 are accommodated in a vacuum glass tube 62 with a substantially cylindrical shape. The cathode 60 is a cold cathode. Specifically, the cathode 60 is a field emission type including an electron emission source that emits an electron beam EB to the anode 61, using a field emission phenomenon. The anode 61 is a fixed anode which is not rotated and whose position is fixed, unlike a rotating anode that is rotated by a rotation mechanism.

A voltage generator 63 applies a tube voltage between the cathode 60 and the anode 61. The electron beam EB is emitted from the cathode 60 to the anode 61 by the application of the tube voltage. Then, the radiation R is emitted from the focus F which is a point of the anode 61 with which the electron beam EB collides.

The radiation tube 55 is accommodated in a housing, which is not illustrated. The housing is provided with a radiation transmission window that transmits the radiation R. The radiation R is emitted from the anode 61 to the outside of the housing through the radiation transmission window. The housing is filled with insulating oil.

Figure 9:
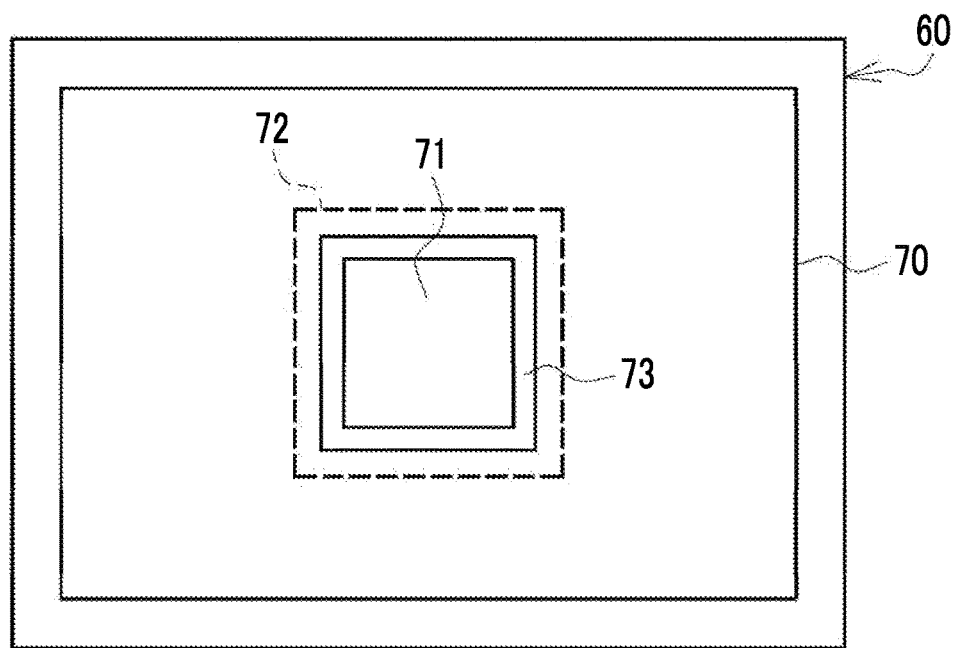
FIG. 9 is a diagram illustrating a cathode.

For example, as illustrated in FIG. 9, the cathode 60 has a structure in which an emitter electrode 71 and a gate electrode 72 are provided on a semiconductor substrate 70. The semiconductor substrate 70 is, for example, crystallized silicon. The emitter electrode 71 is, for example, a cone-shaped carbon nanotube or tungsten nanotube. The emitter electrode 71 is connected to the gate electrode 72. The emitter electrode 71 functions as an emission area for the electron beam EB. That is, the emitter electrode 71 is an example of an "electron emission source" according to the technology of the present disclosure.

A focusing electrode 73 is provided around the emitter electrode 71. The electron beam EB emitted from the emitter electrode 71 is accelerated toward the anode 61 and is focused by the application of a focusing voltage to the focusing electrode 73.

Figure 10:
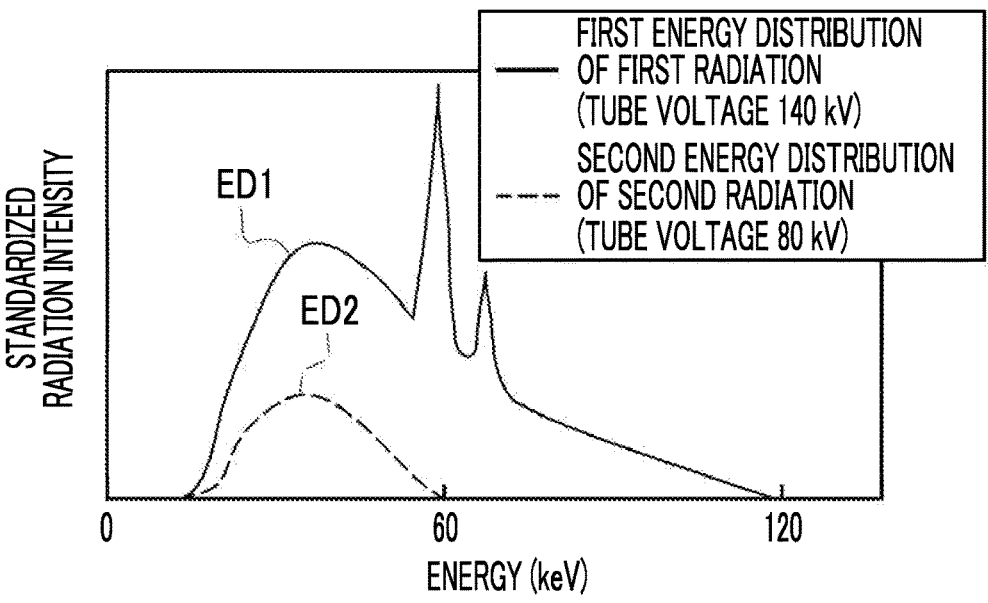
FIG. 10 is a graph illustrating a first energy distribution of first radiation and a second energy distribution of second radiation.

For example, as illustrated in FIG. 10, the radiation tube 55 emits two types of radiation R, that is, first radiation R1 and second radiation R2. The first radiation R1 has a first energy distribution ED1 represented by a solid line. On the other hand, the second radiation R2 has a second energy distribution ED2 represented by a broken line. The first radiation R1 is generated by setting a tube voltage of, for example, 140 kV that is higher than a tube voltage for the second radiation R2. The second radiation R2 is generated by setting a tube voltage of, for example, 80 kV that is lower than the tube voltage for the first radiation R1. The intensity of the second radiation R2 in the second energy distribution ED2 is lower than the intensity of the first radiation R1 in the first energy distribution ED1 due to this level difference between the tube voltages. In short, the second radiation R2 has lower energy than the first radiation R1. In addition, the tube voltage for the first radiation R1 is not limited to 140 kV given as an example. Similarly, the tube voltage for the second radiation R2 is not limited to 80 kV given as an example. In the following description, in a case in which the first energy distribution ED1 and the second energy distribution ED2 do not need to be particularly distinguished from each other, they are collectively referred to as energy distributions ED.

Figure 11:
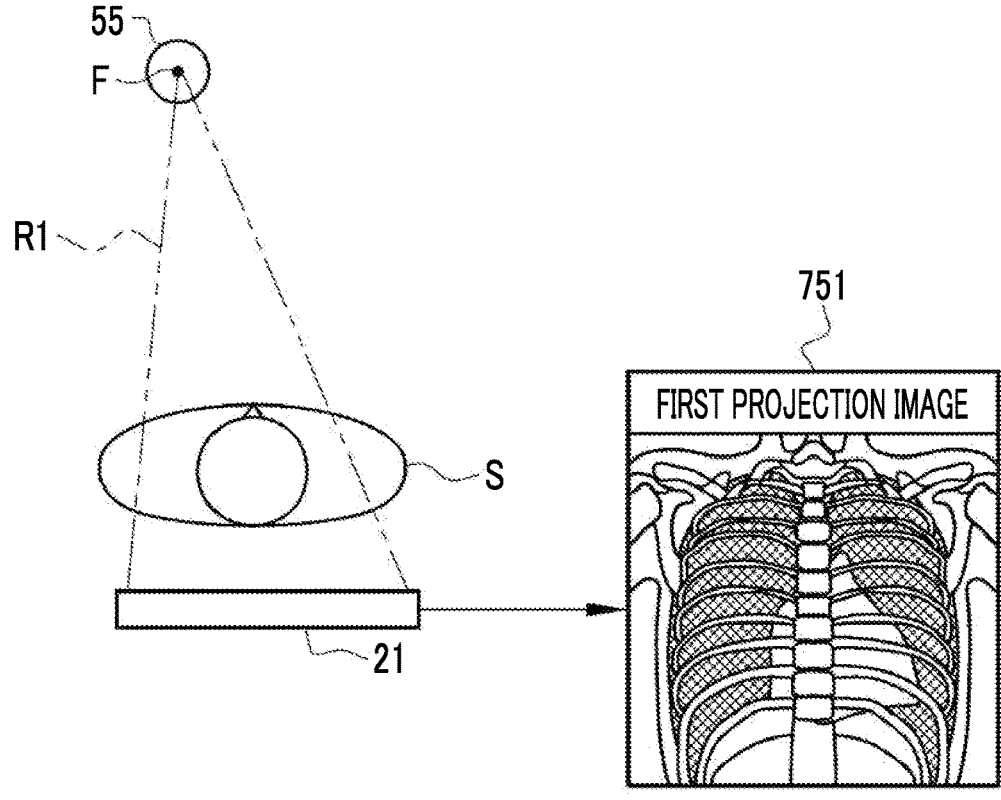
FIG. 11 is a diagram illustrating an aspect in which the first radiation is generated from the radiation tube and a first projection image based on the first radiation transmitted through the subject is output from the radiation detector.
Figure 12:
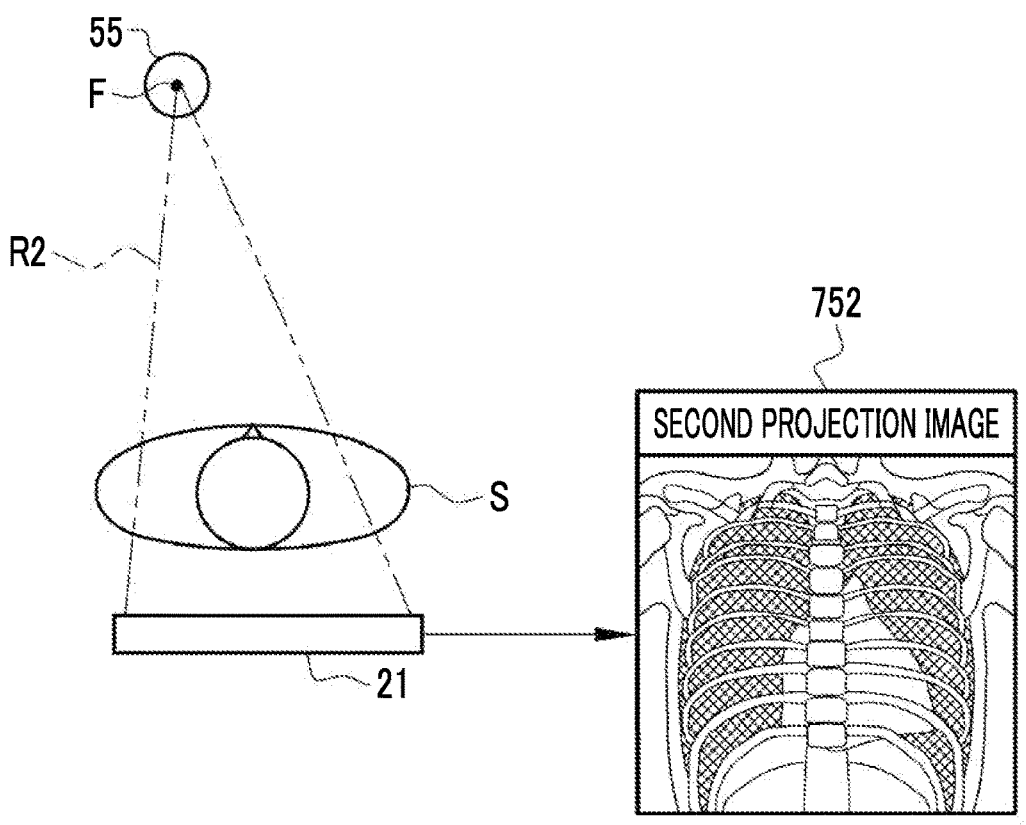
FIG. 12 is a diagram illustrating an aspect in which the second radiation is generated from the radiation tube and a second projection image based on the second radiation transmitted through the subject is output from the radiation detector.

FIG. 11 illustrates an example of an aspect in which the first radiation R1 is generated from the radiation tube 55 and a first projection image 751 based on the first radiation R1 transmitted through the subject S is output from the radiation detector 21. On the other hand, FIG. 12 illustrates an example of an aspect in which the second radiation R2 is generated from the radiation tube 55 and a second projection image 752 based on the second radiation R2 transmitted through the subject S is output from the radiation detector 21. As described above, the CT apparatus 10 can perform ES imaging that directs the radiation source 20 to continuously emit the first radiation R1 and the second radiation R2 having different energy distributions ED as illustrated in FIG. 10 and directs the radiation detector 21 outputs the first projection image 751 based on the first radiation R1 and the second projection image 752 based on the second radiation R2. In the following description, in a case in which the first projection image 751 and the second projection image 752 do not need to be particularly distinguished from each other, they are collectively referred to as projection images 75.

The first projection image 751 and the second projection image 752 include bone tissues, such as the ribs and the backbone, and soft tissues such as the lungs and the stomach. However, the energy levels of the radiation R that are easily absorbed by the bone tissues and the soft tissues are different. Therefore, the bone tissue included in the first projection image 751 and the bone tissue included in the second projection image 752 have different pixel values. In addition, the soft tissue included in the first projection image 751 and the soft tissue included in the second projection image 752 also have different pixel values.

Figure 13:
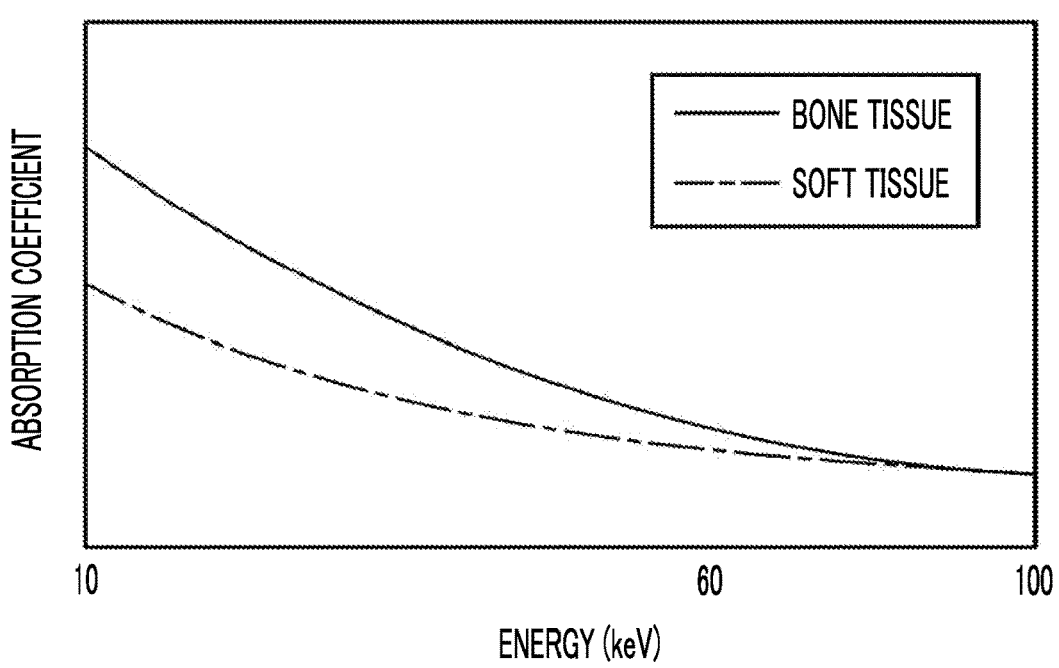
FIG. 13 is a graph illustrating absorption coefficients of a bone tissue and a soft tissue for energy of the radiation.

Specifically, for example, as illustrated in FIG. 13, a difference between an absorption coefficient of the bone tissue and an absorption coefficient of the soft tissue for the radiation R having relatively high energy is small. On the other hand, a difference between an absorption coefficient of the bone tissue and an absorption coefficient of the soft tissue for the radiation R having relatively low energy is large. Here, the radiation R having relatively high energy is the first radiation R1, and the radiation R having relatively low energy is the second radiation R2. Therefore, in the first projection image 751, the ratio of the pixel value of the bone tissue to the pixel value of the soft tissue is low. Conversely, in the second projection image 752, the ratio of the pixel value of the bone tissue to the pixel value of the soft tissue is high.

Figure 14:
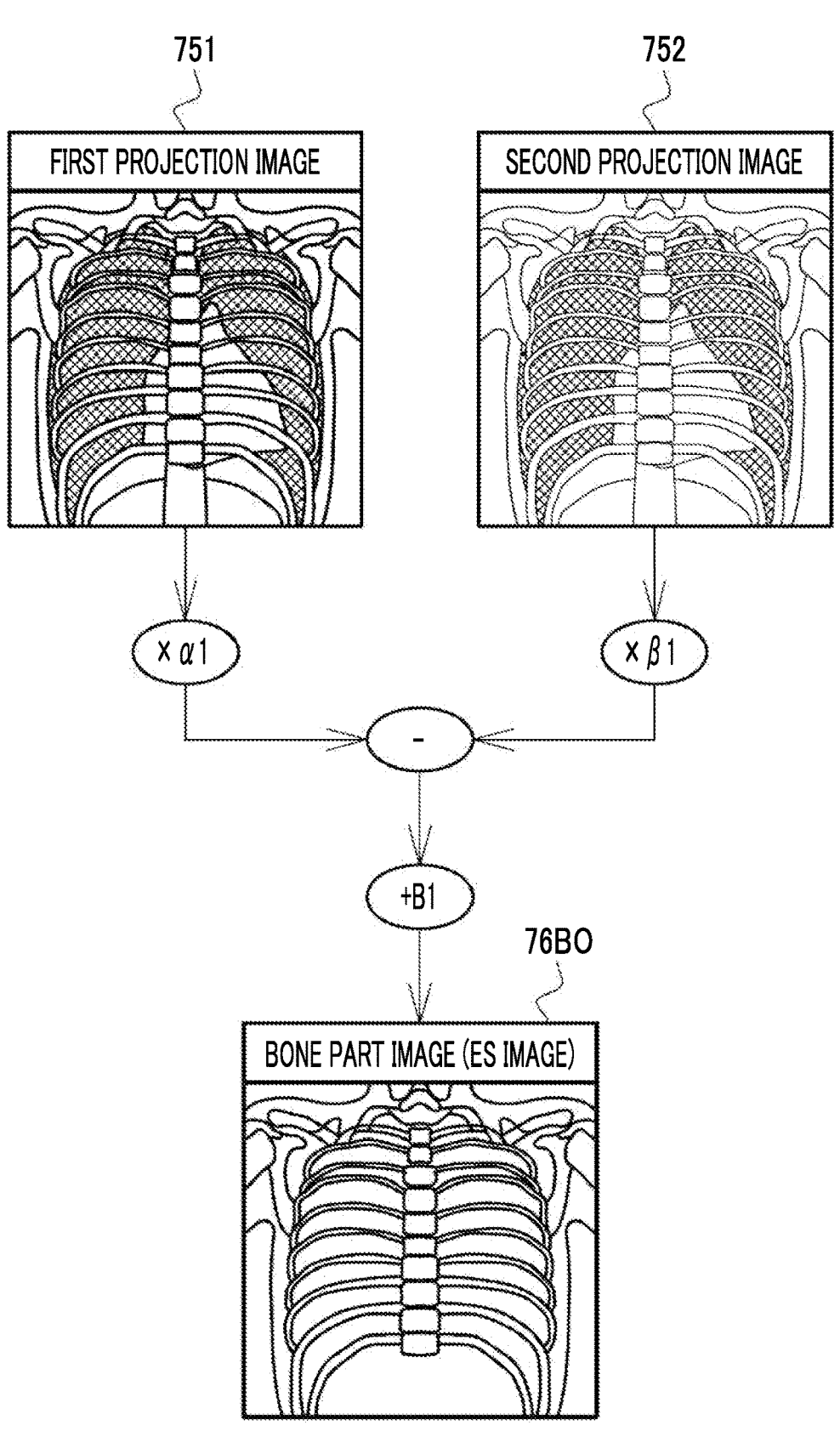
FIG. 14 is a diagram illustrating an aspect in which a bone part image is generated.
Figure 15:
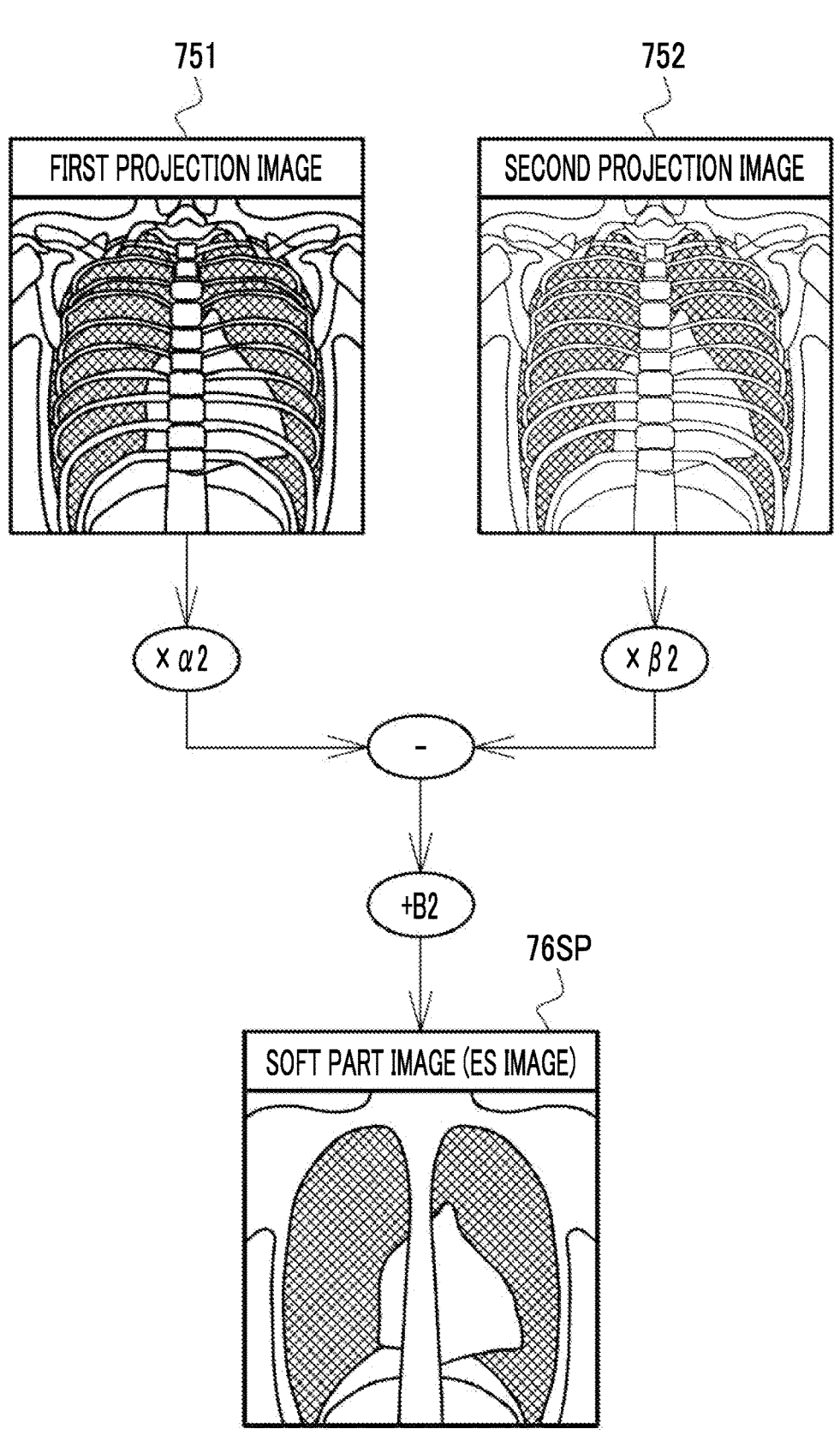
FIG. 15 is a diagram illustrating an aspect in which a soft part image is generated.

FIGS. 14 and 15 illustrate an aspect in which an ES image in which a specific biological tissue in the subject S has been highlighted is generated on the basis of the first projection image 751 and the second projection image 752, using the difference between the absorption coefficients of the bone tissue and the soft tissue for the radiation R illustrated in FIG. 13. FIG. 14 illustrates an aspect in which a bone part image 76BO in which the bone tissue has been highlighted is generated. On the other hand, FIG. 15 illustrates an aspect in which a soft part image 76SP in which the soft tissue has been highlighted is generated. In the following description, in a case in which the bone part image 76BO and the soft part image 76SP do not need to be particularly distinguished from each other, they are collectively referred to as ES images 76.

In FIG. 14, the bone part image 76BO is generated by performing calculation represented by the following Expression (1).

$$BESI = RI1 \times \alpha 1 - RI2 \times \beta 1 + B1 \quad (1)$$

In addition, BESI is a pixel value of the bone part image 76BO, RI1 is a pixel value of the first projection image 751, RI2 is a pixel value of the second projection image 752, $\alpha 1$ and $\beta 1$ are weighting coefficients, and B1 is a bias value.

The weighting coefficients $\alpha 1$ and $\beta 1$ are adjusted to values at which the pixel values of the soft tissues in the first projection image 751 and the second projection image 752 are matched with each other. Therefore, it is possible to generate the bone part image 76BO, in which the soft tissue has been removed and only the bone tissue has been visualized, by multiplying the pixel value RI1 of the first projection image 751 by the weighting coefficient $\alpha 1$, multiplying the pixel value RI2 of the second projection image 752 by the weighting coefficient $\beta 1$, and calculating the difference between the multiplied values.

On the other hand, in FIG. 15, the soft part image 76SP is generated by performing calculation represented by the following Expression (2).

$$SESI = RI1 \times \alpha 2 - RI2 \times \beta 2 + B2 \quad (2)$$

In addition, SESI is a pixel value of the soft part image 76SP, $\alpha 2$ and $\beta 2$ are weighting coefficients, and B2 is a bias value.

Similarly to the weighting coefficients $\alpha 1$ and $\beta 1$, the weighting coefficients $\alpha 2$ and $\beta 2$ are adjusted to values at which the pixel values of the bone tissues in the first projection image 751 and the second projection image 752 are matched with each other. Therefore, it is possible to generate the soft part image 76SP, in which the bone tissue has been removed and only the soft tissue has been visualized, by multiplying the pixel value RI1 of the first projection image 751 by the weighting coefficient $\alpha 2$, multiplying the pixel value RI2 of the second projection image 752 by the weighting coefficient $\beta 2$, and calculating the difference between the multiplied values. Further, in the following description, the process illustrated in FIGS. 14 and 15 is referred to as an ES process.

Figure 16:
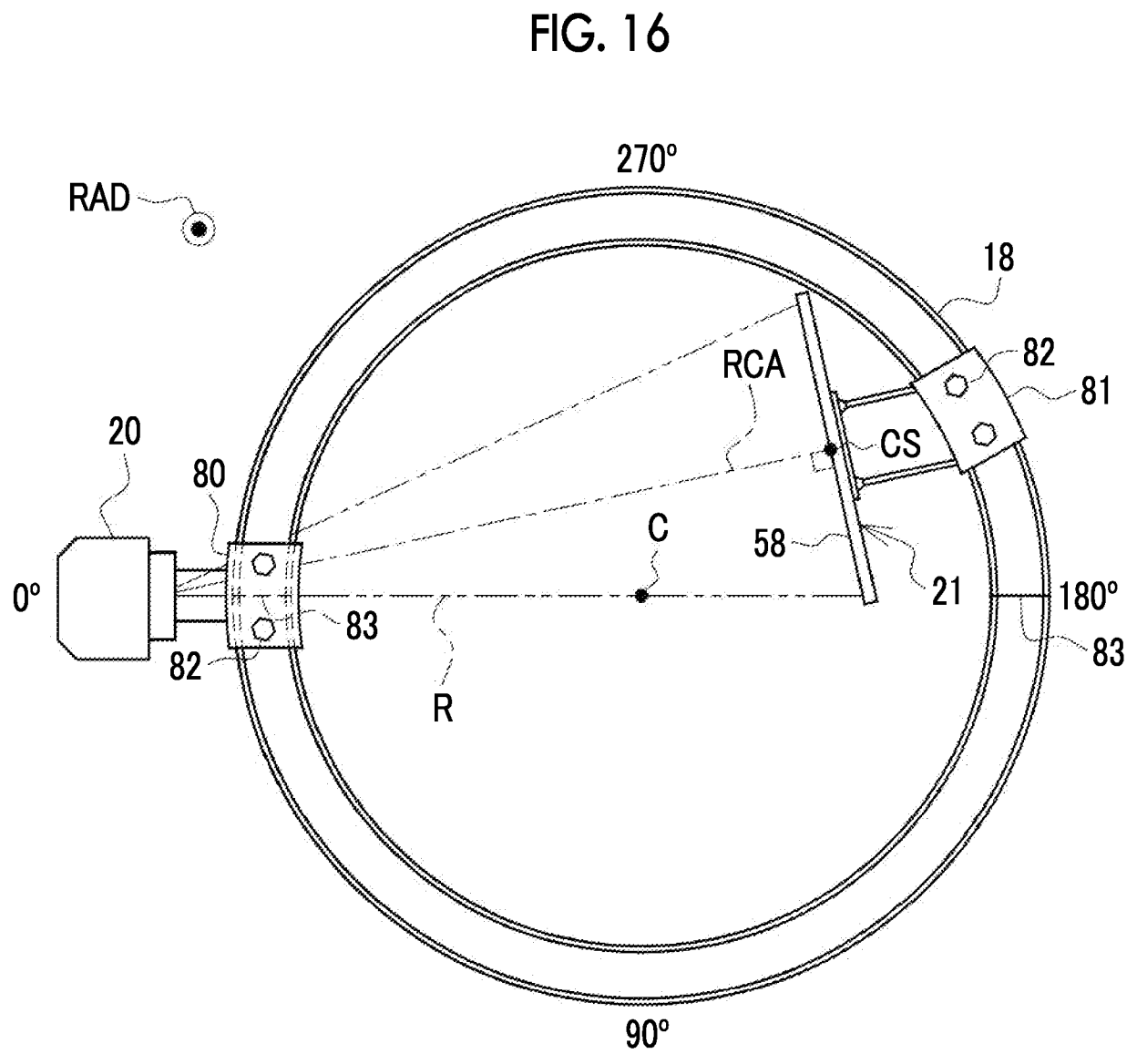

For example, as illustrated in FIG. 16, a central axis RCA of a flux of the radiation R perpendicularly intersects a center point CS of the detection surface 58 of the radiation detector 21. In the following description, it is assumed that the position where the radiation source 20 is disposed is 0° and the positions of every 90° in the counterclockwise direction CCW are 90°, 180°, and 270°.

The radiation source 20 is attached to the frame 18 by an attachment 80. Similarly, the radiation detector 21 is attached to the frame 18 by an attachment 81. The attachments 80 and 81 are fixed to the frame 18 by bolts 82. The radiation source 20 is disposed outside the frame 18, and the radiation detector 21 is disposed inside the frame 18 as viewed from the rotation axis direction RAD.

The frame 18 is formed by joining two semi-annular members by, for example, welding. The attachment 80 is attached to cover one of two opposing joint portions 83 of the frame 18. This attachment of the attachment 80 to the joint portion 83 makes it possible to reinforce the joint portion 83, which is a mechanically weak portion, with the attachment 80.

For example, as illustrated in FIG. 17, the radiation detector 21 is disposed at an offset position that is separated from a reference position facing the radiation source 20 by a preset angle as viewed from the rotation axis direction RAD. Here, the reference position is a position where the central axis RCA of a flux of the radiation R in a case in which the exit opening of the irradiation field limiter 56 is opened to the maximum and the center point CS of the detection surface 58 of the radiation detector 21 intersect perpendicularly. The preset angle at the offset position is half (θ/2) of the emission angle θ in this example.

Figure 18:
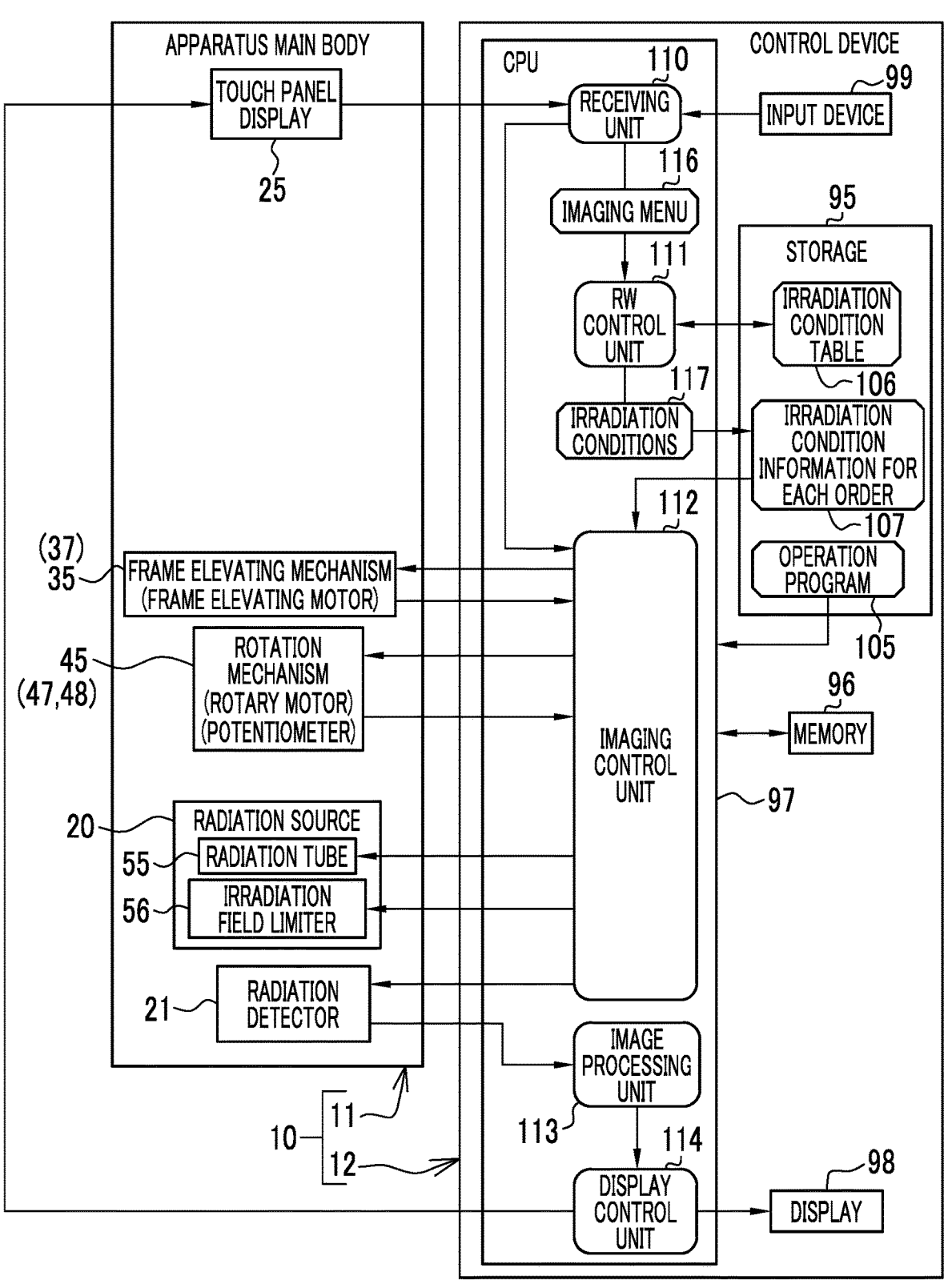
FIG. 18 is a block diagram illustrating a processing unit of a CPU of a control device.

For example, as illustrated in FIG. 18, a computer constituting the control device 12 comprises a storage 95, a memory 96, a central processing unit (CPU) 97, a display 98, an input device 99, and the like.

The storage 95 is a hard disk drive that is provided in the computer constituting the control device 12 or is connected to the computer through a cable or a network. Alternatively, the storage 95 is a disk array in which a plurality of hard disk drives are connected. The storage 95 stores, for example, a control program, such as an operating system, various application programs, and various types of data associated with these programs. In addition, a solid state drive may be used instead of the hard disk drive.

The memory 96 is a work memory for the CPU 97 to perform processes. The CPU 97 loads the program stored in the storage 95 to the memory 96 and performs a process corresponding to the program. Therefore, the CPU 97 controls the overall operation of each unit of the computer. The CPU 97 is an example of a "processor" according to the technology of the present disclosure. In addition, the memory 96 may be provided in the CPU 97.

The display 98 displays various screens. The various screens have operation functions by a graphical user interface (GUI). The computer constituting the control device 12 receives operation instructions input from the input device 99 through various screens. The input device 99 is, for example, a keyboard, a mouse, a touch panel, a microphone for voice input.

An operation program 105 is stored in the storage 95. The operation program 105 is an application program for causing the computer to function as the control device 12. The storage 95 stores, for example, an irradiation condition table 106 and irradiation condition information 107 for each order, in addition to the operation program 105.

In a case in which the operation program 105 is started, the CPU 97 of the control device 12 functions as a receiving unit 110, a read and write (hereinafter, abbreviated to RW)

control unit 111, an imaging control unit 112, an image processing unit 113, and a display control unit 114 in cooperation with, for example, the memory 96.

The receiving unit 110 receives various operation instructions input by the operator through the touch panel display 25 of the apparatus main body 11 and the input device 99. For example, the receiving unit 110 receives an imaging menu 116. The receiving unit 110 outputs the imaging menu 116 to the RW control unit 111.

The RW control unit 111 receives the imaging menu 116 from the receiving unit 110. The RW control unit 111 reads irradiation conditions 117 of the radiation R which correspond to the received imaging menu 116 from the irradiation condition table 106. The RW control unit 111 writes the irradiation conditions 117 read from the irradiation condition table 106 to the irradiation condition information 107 for each order.

The imaging control unit 112 controls the operations of the radiation source 20 (the radiation tube 55 and the irradiation field limiter 56), the frame elevating mechanism 35 (frame elevating motor 37), the rotation mechanism 45 (the rotary motor 47 and the potentiometer 48), and the radiation detector 21. The imaging control unit 112 reads the irradiation conditions 117 from the irradiation condition information 107 for each order. The imaging control unit 112 drives the irradiation field limiter 56 according to the irradiation conditions 117 to adjust the irradiation field. The operator inputs an imaging instruction to the control device 12 through an irradiation switch (not illustrated). In a case in which the imaging instruction is input, the imaging control unit 112 drives the radiation tube 55 according to the irradiation conditions 117 such that the radiation tube 55 generates the radiation R. The imaging control unit 112 outputs the projection image 75 obtained by the detection of the emitted radiation R by the radiation detector 21 from the radiation detector 21 to the image processing unit 113.

The image processing unit 113 receives the projection image 75 from the radiation detector 21. The image processing unit 113 performs various types of image processing on the projection image 75 to generate a tomographic image 120 (see FIG. 21). The image processing unit 113 outputs the tomographic image 120 to the display control unit 114.

The display control unit 114 controls the display of various types of information on the touch panel display 25 and the display 98. The display control unit 114 receives the tomographic image 120 from the image processing unit 113. The display control unit 114 displays the tomographic image 120 on the touch panel display 25 and the display 98.

The imaging menu 116 includes, for example, imaging order identification data (ID) and an imaging technique. The imaging order ID is identification information of an imaging order issued by a doctor who makes a diagnosis using the tomographic image 120. The imaging technique is composed of a posture of the subject S, such as a standing posture or a sitting posture, an imaging part, such as the head, the neck, or the entire spine, and attributes of the subject S such as an adult male, an adult female, and a child.

The imaging order is transmitted from a radiology information system (RIS) (not illustrated) to the control device 12. The control device 12 displays a list of imaging orders on the display 98 under the control of the display control unit 114. The operator browses the list of the imaging orders and checks the content of the list. Then, the control device 12 displays the imaging menu corresponding to the imaging order on the display 98 such that it can be set. The operator operates the input device 99 to select the imaging menu corresponding to the imaging order and to input the imaging menu.

The irradiation conditions 117 are registered in the irradiation condition table 106 for each imaging technique. The irradiation conditions 117 include a tube voltage and a tube current applied to the radiation tube 55 and the irradiation time of the radiation R. As the tube voltage, there are two types of tube voltages for generating two types of radiation R, that is, the first radiation R1 and the second radiation R2. In addition, the irradiation conditions 117 also include the size of the irradiation field. The operator can finely adjust the irradiation conditions 117 by hand. Further, instead of the tube current and the irradiation time, a tube current-irradiation time product, that is, a so-called mAs value may be set as the irradiation condition 117.

The irradiation conditions 117 for each imaging order ID is registered in the irradiation condition information 107 for each order. The imaging control unit 112 reads the irradiation condition 117 corresponding to an imaging order ID of the next imaging from the irradiation condition information 107 for each order and controls the operation of each unit according to the read irradiation conditions 117.

Figure 19:
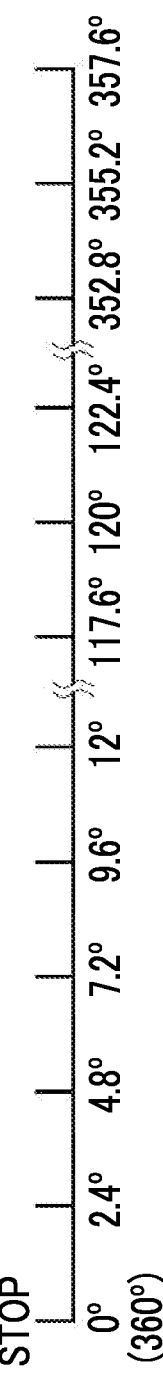
FIG. 19 is a diagram illustrating an acquisition position of a projection image.

For example, as illustrated in FIG. 19, the radiation source 20 emits the radiation R at an angular interval of 2.4°, for example, at 2.4°, 4.8°, 7.2°, . . . , 117.6°, 120°, 122.4°, . . . , 352.8°, 355.2°, and 357.6°, using 0° as a rotation start position and a rotation end position. The radiation detector 21 also outputs the projection image 75 at an angular interval of 2.4°. 2.4° is an example of a "preset angle" according to the technology of the present disclosure. In addition, strictly speaking, the rotation end position is a position that is separated from 0° by an angle of θ in the counterclockwise direction CCW.

Figure 20:
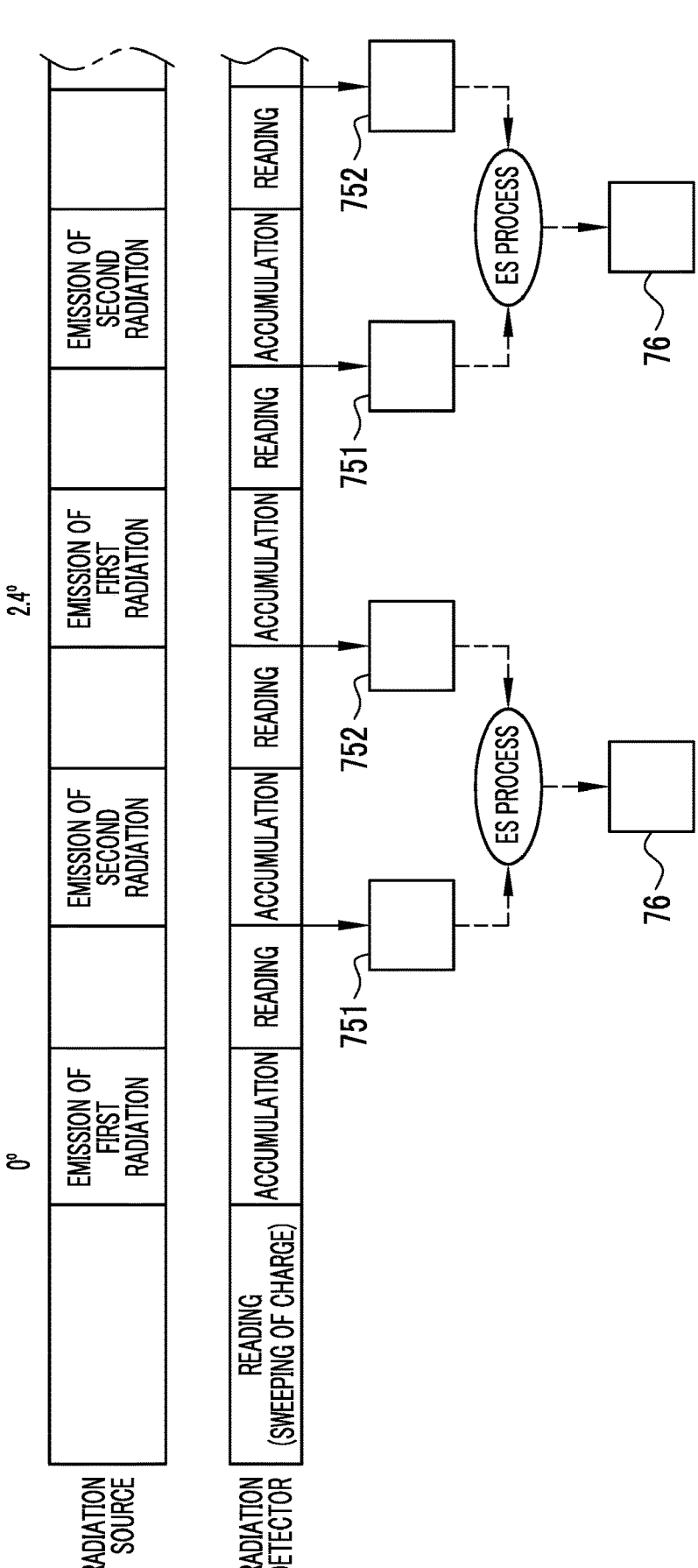
FIG. 20 is a timing chart illustrating the time when the radiation source emits the radiation and the time when the radiation detector reads the projection image.

FIG. 20 is an example of a timing chart illustrating the time when the radiation source 20 emits the radiation R and the time when the radiation detector 21 reads the projection image 75. The imaging control unit 112 directs the radiation detector 21 to perform a reading operation before imaging. This reading operation is an operation of sweeping out unnecessary charge, such as dark charge, accumulated in the pixel 57 during standby and is also called a reset operation.

After directing the radiation detector 21 to perform the reading operation of sweeping out unnecessary charge, the imaging control unit 112 directs the radiation source 20 to emit the first radiation R1. In addition, the imaging control unit 112 directs the radiation detector 21 to perform an accumulation operation. The accumulation operation is an operation of accumulating charge based on the first radiation R1 in the pixel 57. Then, the imaging control unit 112 directs the radiation detector 21 to perform the reading operation and directs the radiation detector 21 to output the first projection image 751 based on the first radiation R1.

Then, the imaging control unit 112 directs the radiation source 20 to emit the second radiation R2 this time. In addition, the imaging control unit 112 directs the radiation detector 21 to perform the accumulation operation of accumulating charge based on the second radiation R2 in the pixel 57. Then, the imaging control unit 112 directs the radiation detector 21 to perform the reading operation and directs the radiation detector 21 to output the second projection image 752 based on the second radiation R2. The irradiation time of the first radiation R1 and the second radiation R2 is, for example, 5 msec to 15 msec.

As described above, the imaging control unit 112 directs the radiation source 20 to alternately and continuously emit the first radiation R1 and the second radiation R2. In addition, the imaging control unit 112 directs the radiation detector 21 to output the first projection image 751 and the second projection image 752. Here, since the radiation source 20 and the radiation detector 21 are rotated, there is a slight deviation between the positions of the radiation source 20 and the radiation detector 21 in a case in which the first radiation R1 is emitted and in a case in which the second radiation R2 is emitted. However, it is assumed that the positions (0°, 2.4°, 4.8°, . . . ) of the radiation source 20 in a case in which the emission of the first radiation R1 is started are the acquisition positions of the first projection image 751 and the second projection image 752. In addition, the second radiation R2 may be emitted first. In addition, after the rotation of the frame 18 is temporarily stopped at each preset angle of 0°, 2.4°, 4.8°, . . . , the first radiation R1 and the second radiation R2 may be alternately and continuously emitted from the radiation source 20.

Here, the "continuous emission of the first radiation and the second radiation" according to the technology of the present disclosure means so-called pulse irradiation in which the first radiation R1 and the second radiation R2 are intermittently and alternately emitted as illustrated in FIG. 20. This is different from so-called continuous irradiation in which the radiation R is continuously emitted from the start to the end of imaging as in the CT apparatus according to the related art.

The image processing unit 113 performs the ES process illustrated in FIG. 14 or FIG. 15 on a set of the first projection image 751 and the second projection image 752 acquired at the same position to generate an ES image 76. Therefore, the ES image 76 for each acquisition position is generated.

Figure 21:
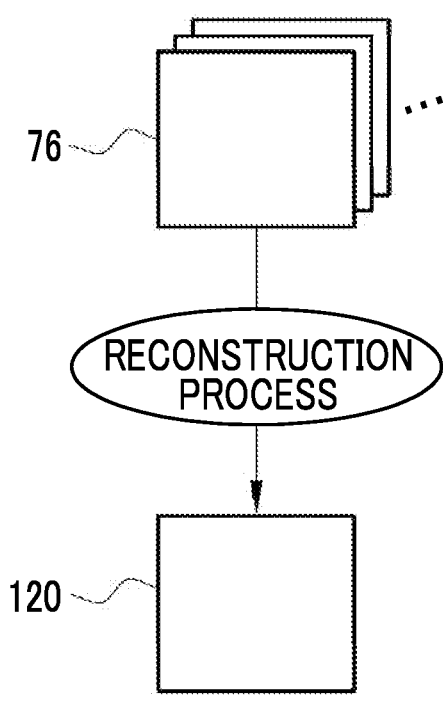
FIG. 21 is a diagram illustrating an outline of a process of an image processing unit.

For example, as illustrated in FIG. 21, the image processing unit 113 performs a reconstruction process on the ES images 76 for each acquisition position to generate the tomographic image 120.

Figure 22:
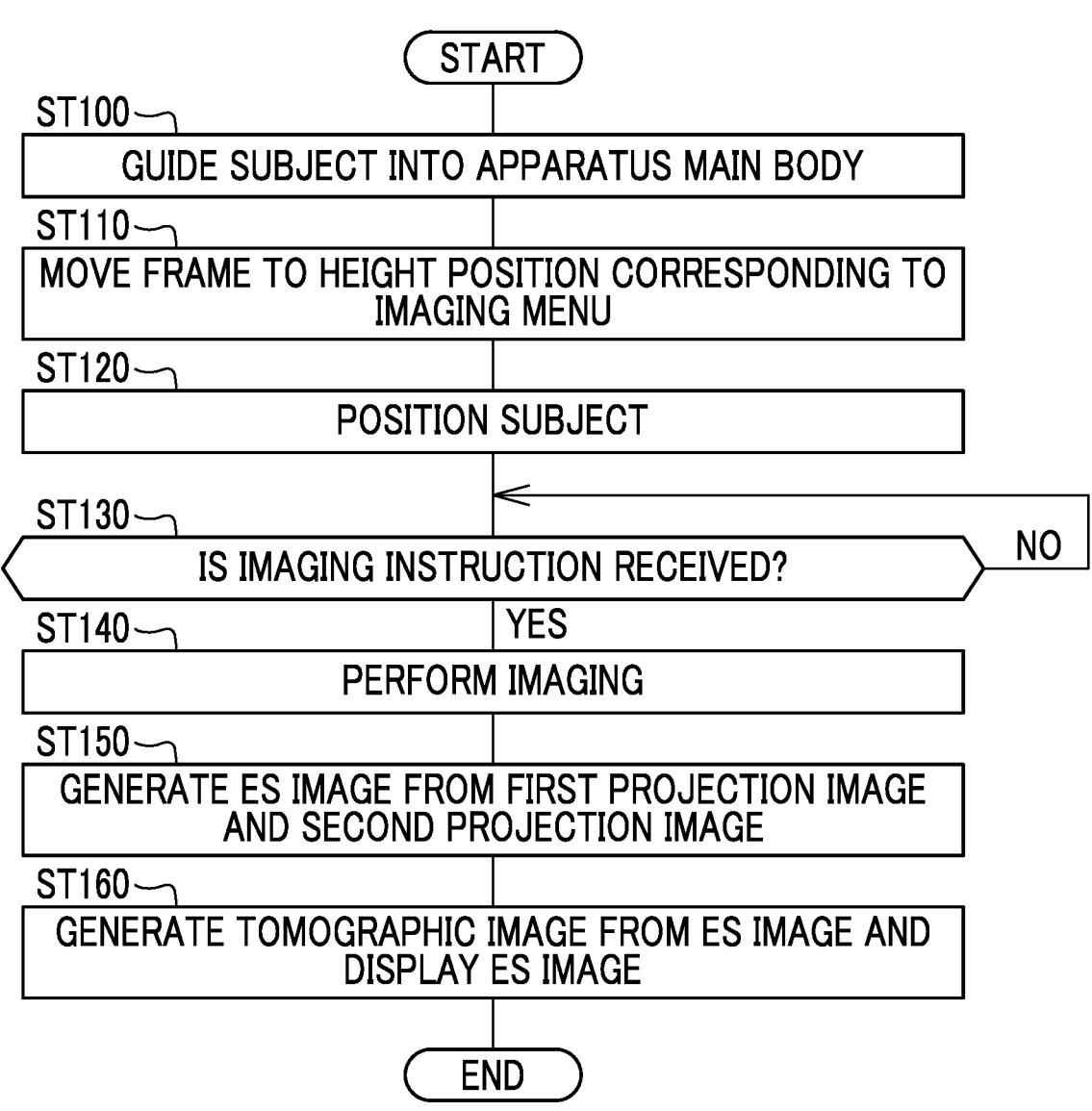
FIG. 22 is a flowchart illustrating an imaging procedure by the CT apparatus.

Next, an example of an imaging procedure by the CT apparatus 10 will be described with reference to a flowchart illustrated in FIG. 22. First, the subject S is guided into the apparatus main body 11 by the operator (Step ST100). Then, the frame elevating mechanism 35 is operated under the control of the imaging control unit 112 to move the frame 18 to a height position corresponding to the imaging menu 116 (Step ST110). Then, the operator positions the subject S (Step ST120). In this case, an irradiation field lamp that is provided in the radiation source 20 is turned on as necessary, and the operator determines whether or not the height position of the frame 18 and the positioning of the subject S are appropriate for imaging. In a case in which the height position of the frame 18 and the positioning of the subject S are not appropriate for imaging, the operator adjusts the height position of the frame 18 or repositions the subject S. In a case in which the height position of the frame 18 and the positioning of the subject S are appropriate for imaging, the operator inputs an imaging instruction through the irradiation switch. The imaging instruction is received by the receiving unit 110 (YES in Step ST130). Then, imaging is performed by the radiation source 20 and the radiation detector 21 (Step ST140).

In the imaging, the rotation mechanism 45 is operated under the control of the imaging control unit 112 to rotate the frame 18 by, for example, 360° in the counterclockwise direction CCW. In the meantime, under the control of the imaging control unit 112, the first radiation R1 and the second radiation R2 are alternately and continuously emitted from the radiation source 20, and the radiation detector 21 outputs the first projection image 751 and the second projection image 752 whenever the radiation is emitted.

After the imaging is ended, the image processing unit 113 generates the ES image 76 from the obtained first and second projection images 751 and 752 (Step ST150) and generates the tomographic image 120 from the ES images 76 (Step ST160). Then, under the control of the display control unit 114, the tomographic image 120 is displayed on, for example, the display 98 and is provided for viewing by the operator (Step ST160).

As described above, the CT apparatus 10 comprises the radiation source 20, the radiation detector 21, the rotation mechanism 45, and the CPU 97. The radiation source 20 emits the radiation R having a quadrangular pyramid shape to the subject S positioned in either the standing posture or the sitting posture. The radiation source 20 includes the radiation tube 55 having the cathode 60 which is a cold cathode. The cathode 60 is a field emission type having the emitter electrode 71 as an electron emission source that emits the electron beam EB using the field emission phenomenon. The radiation detector 21 has a plurality of pixels 57 that detect the radiation R transmitted through the subject S and that are two-dimensionally arranged and outputs the projection image 75 of the subject S. The rotation mechanism 45 rotates the radiation source 20 and the radiation detector 21 around the body axis of the subject S.

The imaging control unit 112 of the CPU 97 directs the radiation source 20 to intermittently and alternately emit the first radiation R1 having the first energy distribution ED1 and the second radiation R2 having the second energy distribution ED2 different from the first energy distribution ED1 whenever the rotation mechanism 45 rotates the radiation source 20 and the radiation detector 21 by the preset angle. The imaging control unit 112 directs the radiation detector 21 to output the first projection image 751 based on the first radiation R1 and the second projection image 752 based on the second radiation R2 which are obtained by the intermittent emission of the first radiation R1 and the second radiation R2, respectively. The image processing unit 113 generates the tomographic image 120 on the basis of the first projection image 751 and the second projection image 752.

Figure 23:
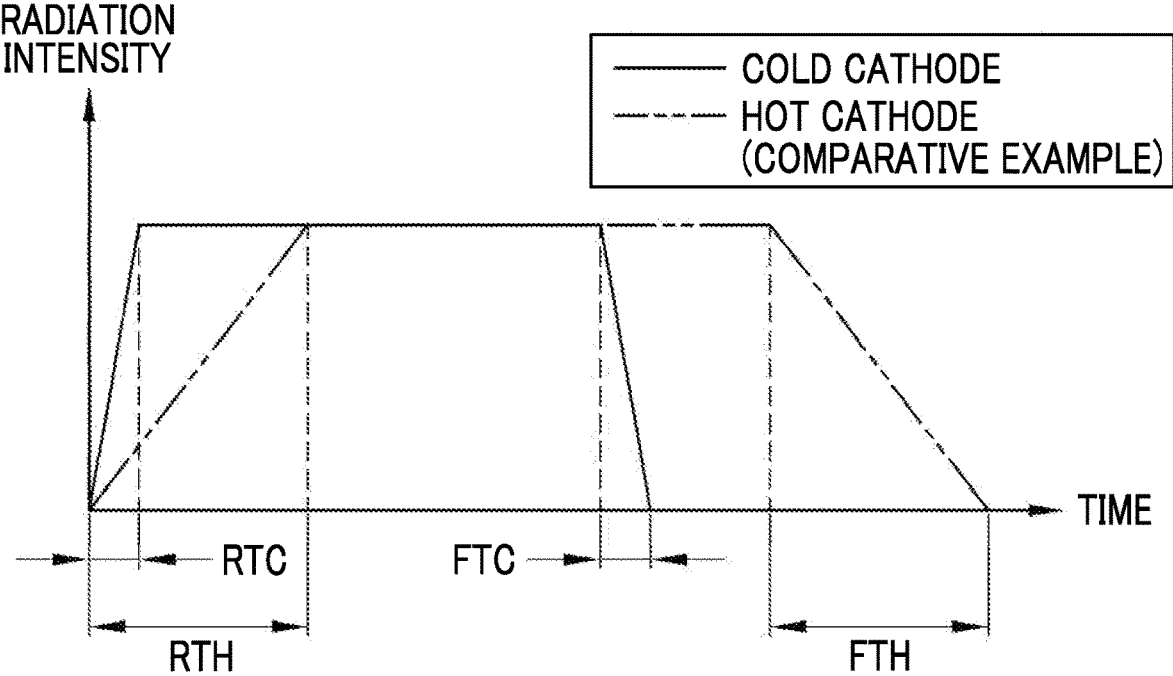
FIG. 23 is a graph illustrating irradiation profiles of radiation emitted from a radiation tube having a cold cathode and radiation emitted from a radiation tube having a hot cathode.

FIG. 23 is a graph illustrating an example of the irradiation profiles of the radiation R (represented by a solid line) emitted from the radiation tube 55 having the cold cathode according to the technology of the present disclosure and the radiation R (represented by a two-dot chain line) emitted from a radiation tube having a hot cathode, such as a cathode having a filament structure that emits thermoelectrons, according to a comparative example. A rise time RTC until the radiation R emitted from the radiation tube 55 having the cold cathode reaches desired radiation intensity is much shorter than a rise time RTH of the radiation R emitted from the radiation tube having the hot cathode. Specifically, while the rise time RTH is about 5 msec, the rise time RTC is as short as about 4 to 5 psec. In addition, a fall time FTC until the radiation R emitted from the radiation tube 55 having the cold cathode falls from the desired radiation intensity to a turn-off state is much shorter than a fall time FTH of the radiation R emitted from the radiation tube having the hot cathode. Specifically, while the fall time FTH is about 5 msec to 90 msec, the fall time FTC is as short as about 4 to 5 psec.

Therefore, in the technology of the present disclosure, the use of the radiation source 20 including the radiation tube 55 having the cold cathode makes it possible to perform switching between the emission of the first radiation R1 and the emission of the second radiation R2 at a higher speed than that in a case in which the radiation source including the radiation tube having the hot cathode is used. Therefore, it is possible to secure the synchronism of the first projection image 751 and the second projection image 752. In addition, it is possible to obtain a larger number of first projection images 751 and second projection images 752 at the preset rotation speed. As a result, it is possible to improve the quality of the tomographic image 120. Further, in a case in which the subject S in the standing posture or the sitting posture, who is more unstable and is more likely to make a body movement than the subject S in the decubitus posture, is imaged, it is possible to reduce the concern that the quality of the tomographic image 120 will deteriorate due to the body movement.

Since the rise time RTC and the fall time FTC are short, the total irradiation time of the radiation R can also be shortened. Therefore, it is possible to obtain the projection image 75 in which blurring caused by rotation has been further suppressed. As a result, it is possible to improve the quality of the tomographic image 120.

The amount of heat generated by the cold cathode is much smaller than the amount of heat generated by the hot cathode. Therefore, a heat dissipation structure is not required, and it is possible to reduce the size of the radiation tube 55. Specifically, the diameter of the radiation tube 55 can be equal to or less than, for example, about 50 mm. Therefore, it is possible to contribute to reducing the size of the radiation source 20.

As illustrated in FIG. 7, the radiation source 20 emits the radiation R having a quadrangular pyramid shape, and the radiation detector 21 has the configuration in which the plurality of pixels 57 detecting the radiation R are two-dimensionally arranged. Therefore, it is possible to complete imaging in a short time, as compared to the CT apparatus according to the related art in which a radiation source emits the radiation R having a fan shape and a radiation detector in which pixels are one-dimensionally arranged detects the radiation R. In addition, the radiation R having a conical shape instead of the quadrangular pyramid shape may be emitted.

As illustrated in FIGS. 1, 2, and 4, the subject S is positioned in either the standing posture or the sitting posture. Therefore, it is possible to meet the demand to observe soft tissues, such as the lungs, in a natural state in which gravity is applied or to observe joints, such as hip joints, in a state in which gravity is applied and a load is applied.

Figure 24:
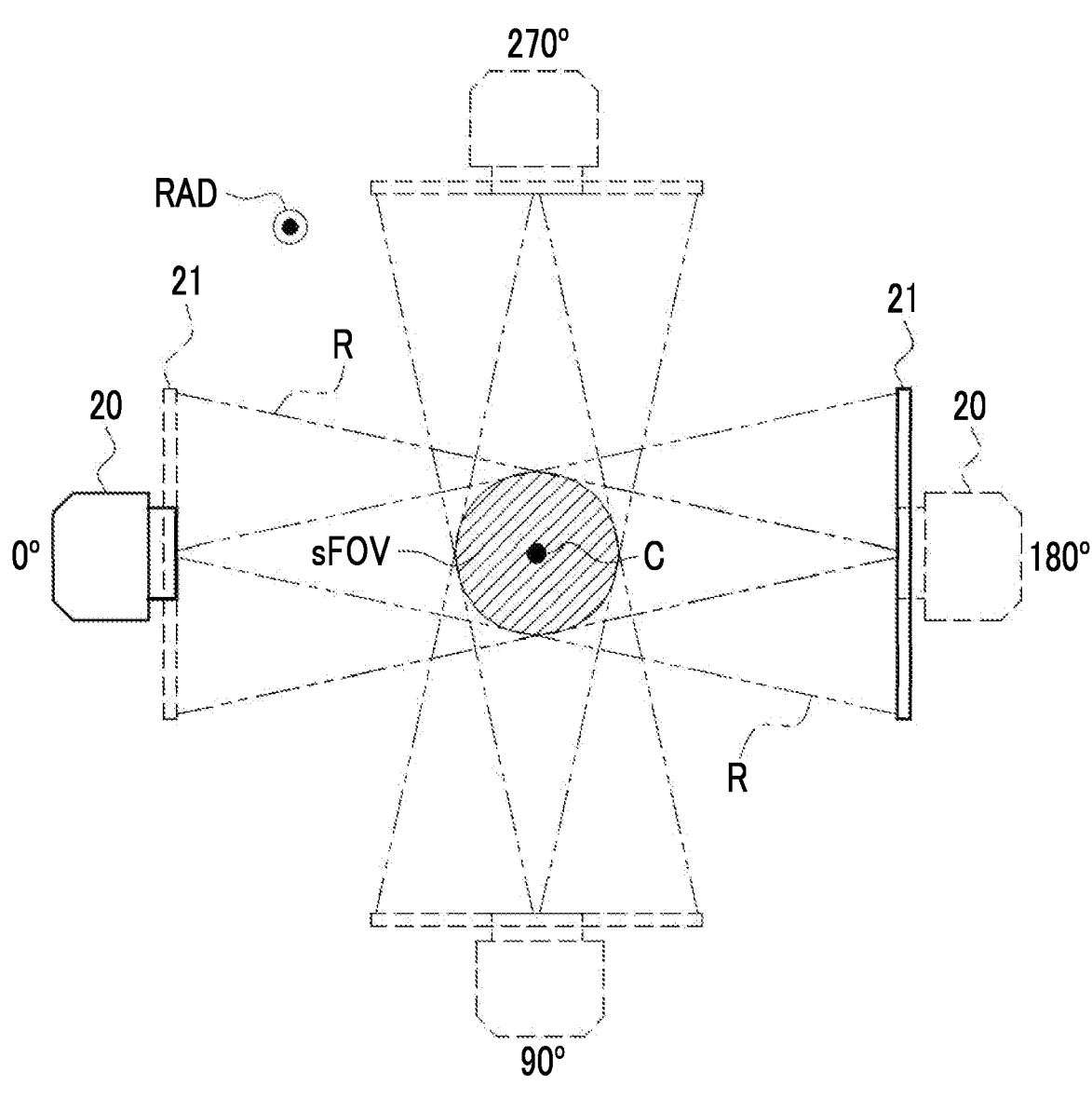
FIG. 24 is a diagram illustrating a scan field of view in a case in which the radiation detector is located at the reference position.
Figure 25:
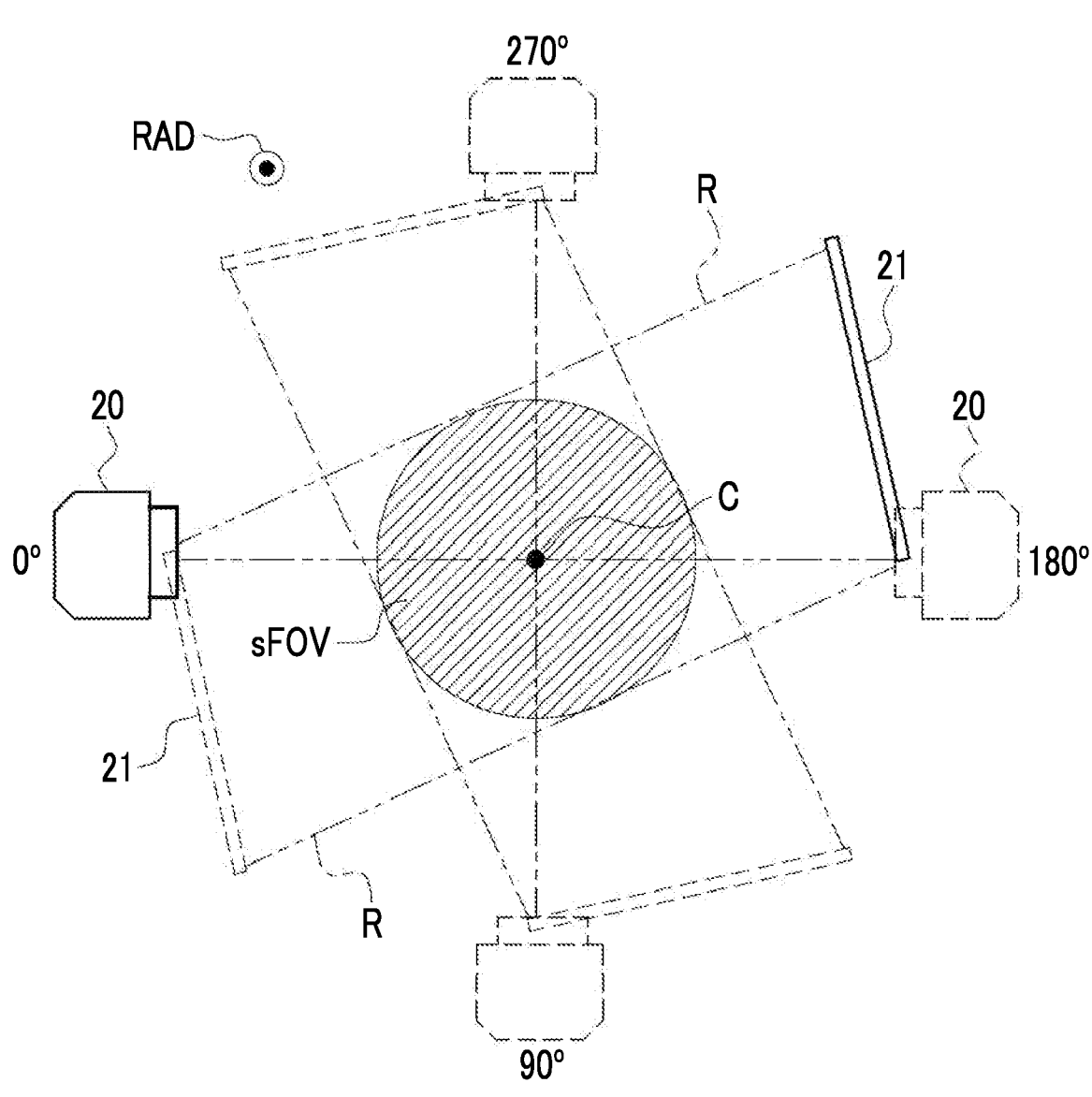
FIG. 25 is a diagram illustrating a scan field of view in a case in which the radiation detector is located at the offset position.

Here, as illustrated in FIG. 24, in a case in which the radiation detector 21 is disposed at the reference position, the region to be scanned does not change with a rotation of 360°. Therefore, a scan field of view sFOV stays in a relatively small region as represented by hatching. On the other hand, as illustrated in FIG. 25, in a case in which the radiation detector 21 is disposed at the offset position, the region to be scanned changes with a rotation of 360°. Therefore, the scan field of view sFOV is a relatively large region as represented by hatching. Therefore, as illustrated in FIG. 17, in a case in which the radiation detector 21 is disposed at the offset position that is separated from the reference position facing the radiation source 20 by the preset angle as viewed from the rotation axis direction RAD, it is possible to widen the scan field of view sFOV, as compared to a case in which the radiation detector 21 is disposed at the reference position.

The radiation source 20 and the radiation detector 21 are held in the frame 18, and the subject S is positioned in the frame 18. As illustrated in FIG. 16, the radiation source 20 is disposed outside the frame 18, and the radiation detector 21 is disposed inside the frame 18, as viewed from the rotation axis direction RAD. The scan field of view sFOV increases as the radiation source 20 is further away from the subject S and as the radiation detector 21 is closer to the subject S. Therefore, in a case in which the radiation source 20 is disposed outside the frame 18 in which the subject S is positioned and the radiation detector 21 is disposed inside the frame 18, it is possible to widen the scan field of view sFOV.

As illustrated in FIG. 7, the widths WA and WB of the detection surface 58 for the radiation R in the radiation detector 21 are equal to or greater than 300 mm. Therefore, it is possible to secure a relatively wide scan field of view sFOV.

Second Embodiment

Figure 26:
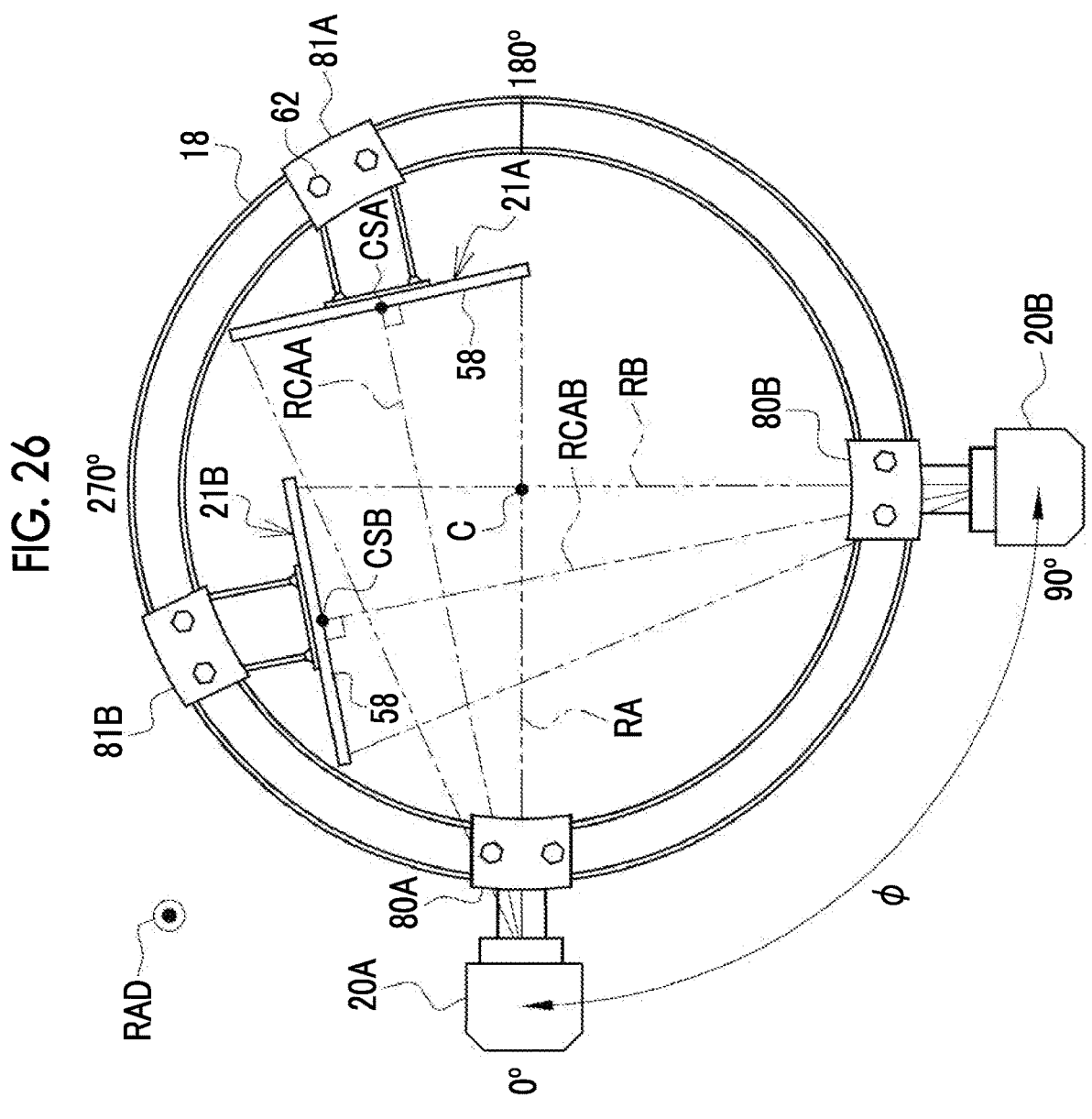
FIG. 26 is a diagram illustrating a second embodiment comprising two imaging units.
Figure 27:
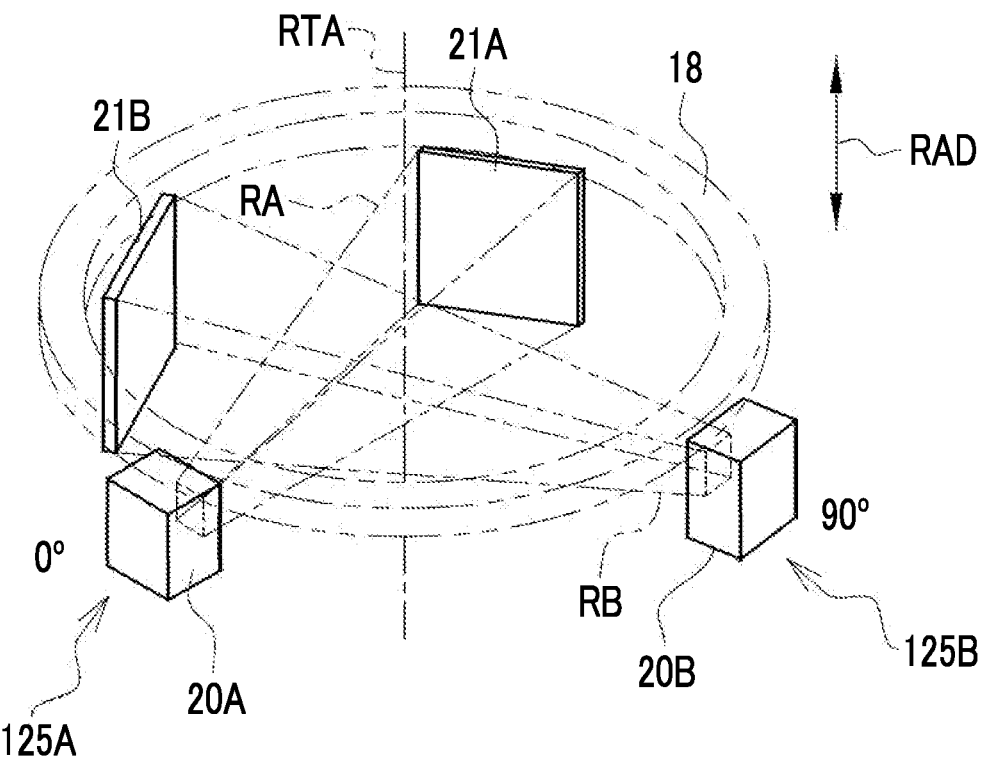
FIG. 27 is a diagram illustrating positions where the imaging units are disposed.

For example, as illustrated in FIGS. 26 and 27, in a second embodiment, two imaging units of an imaging unit 125A and an imaging unit 125B are provided. The imaging unit 125A is composed of a set of a radiation source 20A and a radiation detector 21A, and the imaging unit 125B is composed of a set of a radiation source 20B and a radiation detector 21B. The radiation source 20A is disposed at a position of 0° similarly to the radiation source 20 according to the first embodiment. The radiation source 20B is disposed at a position that is separated from the radiation source 20A by an angle φ. The radiation detectors 21A and 21B are disposed at positions corresponding to the positions where the radiation sources 20A and 20B are disposed. Therefore, the imaging unit 125A and the imaging unit 125B have different phases in the rotation direction. In addition, φ is 90° in this example. Further, both the radiation detectors 21A and 21B are disposed at the offset positions illustrated in FIG. 17.

A central axis RCAA of a flux of radiation RA emitted from the radiation source 20A perpendicularly intersects a center point CSA of the detection surface 58 of the radiation detector 21A. Further, a central axis RCAB of a flux of radiation RB emitted from the radiation source 20B perpendicularly intersects a center point CSB of the detection surface 58 of the radiation detector 21B.

The radiation source 20A is attached to the frame 18 by an attachment 80A. Similarly, the radiation detector 21A is attached to the frame 18 by an attachment 81A. Further, the radiation source 20B is attached to the frame 18 by an attachment 80B, and the radiation detector 21B is attached to the frame 18 by an attachment 81B. Therefore, the imaging unit 125A and the imaging unit 125B are rotated together in the same rotation direction by the rotation mechanism 45 while maintaining the positional relationship therebetween.

For example, as illustrated in FIG. 28, the radiation source 20B is raised and lowered in the rotation axis direction RAD by a radiation source elevating mechanism 130. The radiation source elevating mechanism 130 is composed of, for example, a guide rail 131 and a radiation source elevating motor 132. The guide rail 131 is composed of a first portion 131A that extends from the attachment 80B to the outside of the frame 18 and a second portion 131B that is bent at a right angle from the first portion 131A and extends downward along the rotation axis direction RAD. The second portion 131B has a length capable of covering the half body (the upper half of the body above the waist and the lower half of the body below the waist) of a general adult male. Here, the "length capable of covering the half body of the general adult male" is, for example, a length of about 100 cm in a case in which 200 cm is considered as the maximum height although there is a race or individual difference. This setting of the length of the second portion 131B to the "length capable of covering the half body of the general adult male" makes it possible to perform imaging and diagnosis without omitting the entire half body. It is possible to reduce the concern that re-imaging will be required due to the omission of imaging, which causes an increase in imaging time and an increase in the radiation exposure of the subject S. In consideration of a case in which the whole body of the subject S is imaged instead of the half body, the length of the second portion 131B may be set to be greater than about 100 cm. In addition, in FIG. 28, the first radiation source 20A and the first radiation detector 21A are not illustrated in order to avoid complication.

The radiation source 20B is attached to the second portion 131B. The raising of the radiation source 20B is regulated by the first portion 131A. In addition, a stopper 133 is provided at a lower end of the second portion 131B. The lowering of the radiation source 20B is regulated by the stopper 133. The radiation source 20B can be raised and lowered between an upper end position determined by the first portion 131A and a lower end position determined by the stopper 133.

The radiation source elevating motor 132 is rotationally driven to move the radiation source 20B along the second portion 131B. The height position of the radiation source 20B is determined from the rotation direction and rotation speed of the radiation source elevating motor 132.

The radiation detector 21B is raised and lowered in the rotation axis direction RAD by a detector elevating mechanism 140. The detector elevating mechanism 140 is composed of, for example, a guide rail 141 and a detector elevating motor 142. The guide rail 141 extends straight downward from the attachment 81B along the rotation axis direction RAD. The guide rail 141 has a length capable of covering the half body of the general adult male, similarly to the second portion 131B of the guide rail 131.

An elevating box 143 is attached to the guide rail 141. The detector elevating motor 142 is provided in the elevating box 143. The radiation detector 21B is attached to the elevating box 143 through an arm 144. The arm 144 is an elongated rod that extends from a central portion of the elevating box 143 to the inside of the frame 18.

Stoppers 145 and 146 are provided at upper and lower ends of the guide rail 141, respectively. The raising of the radiation detector 21B is regulated by the stopper 145, and the lowering of the radiation detector 21B is regulated by the stopper 146. The radiation detector 21B can be raised and lowered between an upper end position determined by the stopper 145 and a lower end position determined by the stopper 146. The upper end position and the lower end position of the radiation detector 21B correspond to the upper end position and the lower end position of the radiation source 20B, respectively.

The detector elevating motor 142 is rotationally driven in operative association with the radiation source elevating motor 132 to move the elevating box 143 and thus the radiation detector 21B along the guide rail 141. The height position of the radiation detector 21B is determined from the rotation direction and rotation speed of the detector elevating motor 142.

The radiation source elevating mechanism 130 and the detector elevating mechanism 140 are not provided in the radiation source 20A and the radiation detector 21A which are not illustrated in FIG. 28. Therefore, the radiation source 20A and the radiation detector 21A are not raised and lowered in the rotation axis direction RAD. The height positions of the radiation source 20A and the radiation detector 21A are fixed to the upper end positions (see FIGS. 29 and 30).

While the height positions of the radiation source 20A and the radiation detector 21A are fixed to the upper end positions, the height positions of the radiation source 20B and the radiation detector 21B are changed by the radiation source elevating mechanism 130 and the detector elevating mechanism 140, respectively. That is, an interval between the imaging unit 125A and the imaging unit 125B in the rotation axis direction RAD changes. Therefore, the CT apparatus 10 can perform imaging with a relatively large interval between the imaging unit 125A and the imaging unit 125B in the rotation axis direction RAD or can perform imaging with a relatively small interval between the imaging unit 125A and the imaging unit 125B in the rotation axis direction RAD. The radiation source elevating mechanism 130 and the detector elevating mechanism 140 are examples of a "displacement mechanism" according to the technology of the present disclosure.

Figure 29:
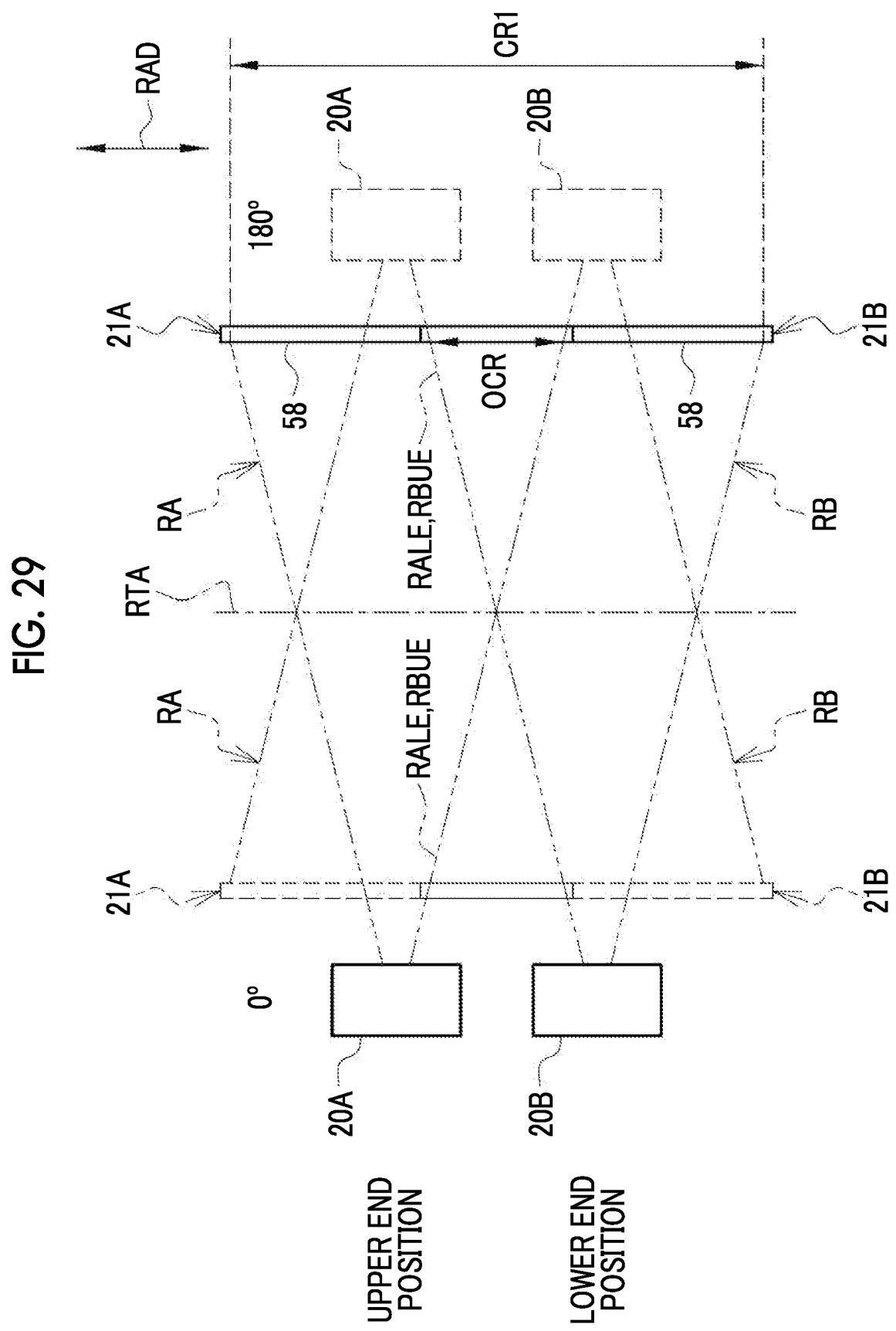
FIG. 29 is a diagram illustrating a flux of radiation in a case in which one imaging unit is located at an upper end position and the other imaging unit is located at a lower end position.

For example, as illustrated in FIG. 29, in a case in which the radiation source 20B and the radiation detector 21B are located at the lower end positions, a lower end RALE of the flux of the radiation RA is matched with an upper end RBUE of the flux of the radiation RB. In other words, the upper end position and the lower end position in this example are positions where the lower end RALE of the flux of the radiation RA is matched with the upper end RBUE of the flux of the second radiation RB. In this case, an imaging range CR1 is a range having a width that is about 1.5 times the width WA of the detection surface 58 of one radiation detector 21 in the rotation axis direction RAD. That is, the imaging range CR1 is a range that exceeds the width WA. In addition, FIG. 29 illustrates the radiation RA and the radiation RB in a case in which the radiation sources 20A and 20B and the radiation detectors 21A and 21B are located at each of the positions of 0° and 180° illustrated in FIG. 26 for convenience of explanation. Further, in FIG. 29, the radiation detectors 21A and 21B are not offset unlike FIG. 17 in order to avoid complication. The same is also applied to FIG. 30 and the like which will be described below.

The imaging unit 125A and the imaging unit 125B have an overlapping imaging range as represented by letters OCR. The imaging control unit 112 disposes the imaging unit 125A and the imaging unit 125B at the positions where the overlapping imaging range OCR can be secured. That is, the imaging control unit 112 sets the interval between the imaging unit 125A and the imaging unit 125B in the rotation axis direction RAD such that the overlapping imaging range OCR occurs between a first projection image 751A and a second projection image 752A and between a first projection image 751B and a second projection image 752B (see FIG. 32) obtained from the imaging unit 125A and the imaging unit 125B.

Figure 30:
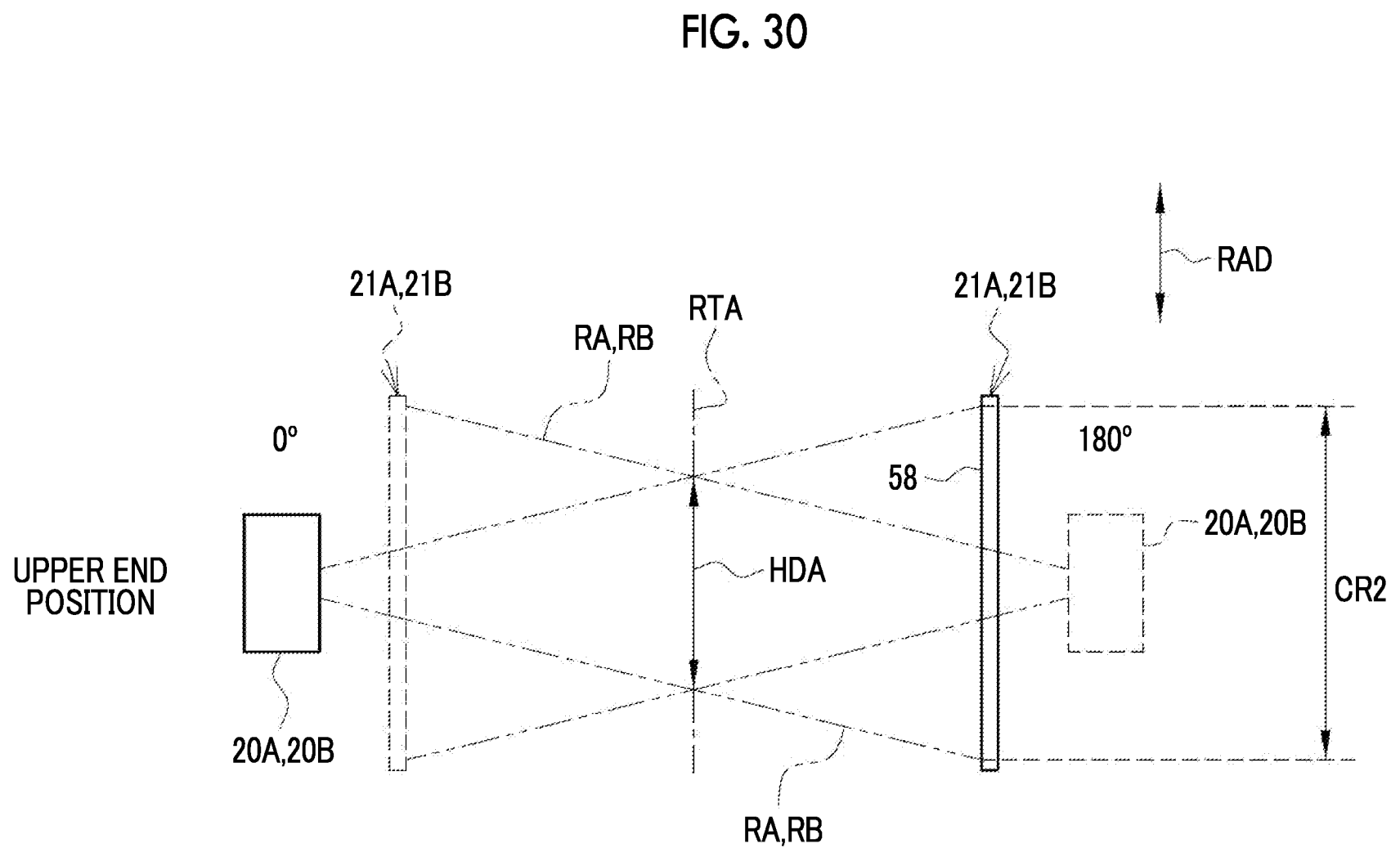

For example, as illustrated in FIG. 30, in a case in which the radiation source 20B and the radiation detector 21B are located at the upper end positions, the flux of the radiation RA is matched with the flux of the radiation RB. In this case, a second imaging range CR2 is a range that is matched with the width WA of the detection surface 58 of one radiation detector 21 in the rotation axis direction RAD. That is, the second imaging range CR2 is a range within the width WA. A region which is represented by an arrow and letters HDA and which is irradiated with the radiation RA and the radiation RB at any rotation angle is a region in which a high-definition tomographic image 120 can be obtained (hereinafter, referred to as a high-definition drawing region). The width of high-definition drawing region HDA in the rotation axis direction RAD is, for example, 200 mm to 300 mm. Further, in this embodiment, the term "match" means match including an error that is generally allowed in the technical field to which the technology of the present disclosure belongs and does not deviate from the gist of the technology of the present disclosure, in addition to perfect match.

The aspect illustrated in FIG. 29 is an example of the imaging in which the interval between the imaging unit 125A and the imaging unit 125B in the rotation axis direction RAD is relatively large. On the other hand, the aspect illustrated in FIG. 30 is an example of the imaging in which the interval between the imaging unit 125A and the imaging unit 125B in the rotation axis direction RAD is relatively small.

Figure 31:
FIG. 31 is a diagram illustrating an acquisition position of a projection image in the case of the aspect illustrated in FIG. 30.

In the case of the aspect illustrated in FIG. 29, the radiation sources 20A and 20B emit the radiation R at an angular interval of 2.4°, using 0° as the rotation start position and the rotation end position, as in the case illustrated in FIG. 19 in the first embodiment. The radiation detectors 21A and 21B also output the projection images 75 at an angular interval of 2.4°. On the other hand, in the case of the aspect illustrated in FIG. 30, for example, the radiation sources 20A and 20B emit the radiation R at an angular interval of 2.4°, for example, at 2.4°, 4.8°, 7.2°, . . . , 117.6°, 120°, 122.4°, . . . , 264°, and 266.4°, using 0° and 268.8° as the rotation start position and the rotation end position, respectively, as illustrated in FIG. 31. The radiation detectors 21A and 21B also output the projection images 75 at an angular interval of 2.4°. In addition, strictly speaking, the rotation end position is a position that is separated from 268.8° by an angle of θ in the counterclockwise direction CCW.

In the case of the aspect illustrated in FIG. 30, the height positions of the imaging units 125A and 125B are aligned with the same upper end position. Further, as illustrated in FIG. 26, the radiation source 20A and the radiation source 20B are disposed at the positions that are separated by an angle of 90°. Therefore, in a case in which the frame 18 is rotated by about 270°, an angular range of 360° is covered.

In the case of the aspect illustrated in FIG. 30, the imaging unit 125A is in charge of imaging in an angular range of 0° to 268.8°, and the imaging unit 125B is in charge of imaging in an angular range of 90° to 358.8°. That is, the imaging of the entire circumference around the body axis of the subject S is shared by the imaging unit 125A and the imaging unit 125B. The projection images 75 obtained by the imaging unit 125A and the imaging unit 125B in the overlapping angular range, here, an angular range of 90° to 268.8° are discarded without being used for generating the tomographic image 120. In addition, the projection images 75 obtained by the imaging unit 125A and the imaging unit 125B in the overlapping angular range may be used for checking the accuracy of the time when the projection images 75 are captured.

FIG. 32 is an example of a timing chart illustrating the time when the radiation sources 20A and 20B emit the radiation R and the time when the radiation detectors 21A and 21B read the projection images 75 in the second embodiment. In addition, in FIG. 32, the radiation source 20A is referred to as a "radiation source A", the radiation detector 21A is referred to as a "radiation detector A", the radiation source 20B is referred to as a "radiation source B", and the radiation detector 21B is referred to as a "radiation detector B".

As illustrated in FIG. 32, the imaging control unit 112 directs the radiation detectors 21A and 21B to perform the reading operation of sweeping out unnecessary charge prior to imaging, as in the first embodiment.

After directing the radiation detectors 21A and 21B to perform the reading operation of sweeping out unnecessary charge, the imaging control unit 112 directs the radiation sources 20A and 20B to emit first radiation R1A and first radiation R1B at the same time. In addition, the imaging control unit 112 directs the radiation detectors 21A and 21B to perform the accumulation operation. The first radiation R1A and the first radiation R1B are the radiation R having the first energy distribution ED1, similarly to the first radiation R1 according to the first embodiment. Then, the imaging control unit 112 directs the radiation detectors 21A and 21B to perform the reading operation and directs the radiation detectors 21A and 21B to output the first projection image 751A based on the first radiation R1A and the first projection image 751B based on the first radiation R1B.

Then, the imaging control unit 112 directs the radiation sources 20A and 20B to emit second radiation R2A and second radiation R2B at the same time. In addition, the imaging control unit 112 directs the radiation detectors 21A and 21B to perform the accumulation operation. Then, the imaging control unit 112 directs the radiation detectors 21A and 21B to perform the reading operation and directs the radiation detectors 21A and 21B to output the second projection image 752A based on the second radiation R2A and the second projection image 752B based on the second radiation R2B. In addition, the "same time" means the same time including an error which is generally allowed in the technical field to which the technology of the present disclosure belongs and is not contrary to the gist of the technology of the present disclosure, in addition to the exact same time.

As described above, the imaging control unit 112 directs the radiation source 20A to alternately and continuously emit the first radiation R1A and the second radiation R2A and directs the radiation source 20B to alternately and continuously emit the first radiation R1B and the second radiation R2B. In addition, the imaging control unit 112 directs the radiation detectors 21A and 21B to output the first projection images 751A and 751B and the second projection images 752A and 752B.

Figure 33:
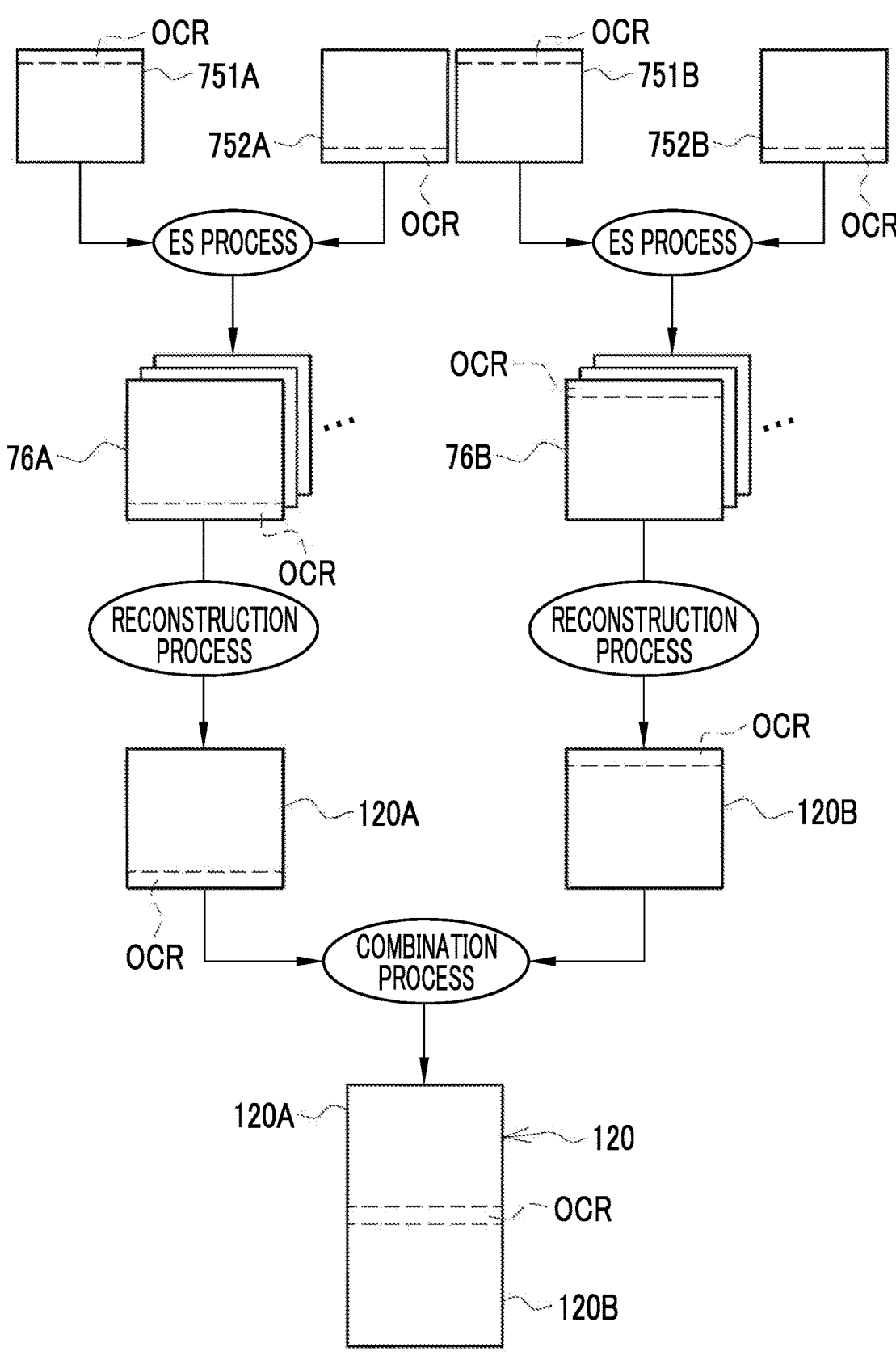
FIG. 33 is a diagram illustrating an outline of a process of an image processing unit according to the second embodiment.

For example, as illustrated in FIG. 33, in the case of the aspect illustrated in FIG. 29, the image processing unit 113 performs the ES process on a set of the first projection image 751A and the second projection image 752A acquired at the same position to generate an ES image 76A. In addition, the image processing unit 113 performs the ES process on a set of the first projection image 751B and the second projection image 752B acquired at the same position to generate an ES image 76B. Therefore, the ES images 76A and 76B for each acquisition position are generated.

The image processing unit 113 performs the reconstruction process on the ES images 76A to generate a tomographic image 120A. In addition, the image processing unit 113 performs the reconstruction process on the ES images 76B to generate a tomographic image 120B. The image processing unit 113 registers the tomographic images 120A and 120B on the basis of the overlapping imaging range OCR and combines the tomographic images 120A and 120B to generate a final tomographic image 120 for diagnosis. In this case, a process may be performed using a sigmoid function to smoothly connect the tomographic images 120A and 120B in the overlapping imaging range OCR.

In the case of the aspect illustrated in FIG. 30, the image processing unit 113 generates the ES image 76A from the first projection image 751A and the second projection image 752A acquired at the same position in an angular range of 0° to 268.8° and generates the ES image 76B from the first projection image 751B and the second projection image 752B acquired at the same position in an angular range of 90° to 358.8°. Then, the final tomographic image 120 for diagnosis is generated from the ES images 76A and 76B.

As described above, in the second embodiment, the imaging unit 125A that is composed of a set of the radiation source 20A and the radiation detector 21A and the imaging unit 125B that is composed of a set of the radiation source 20B and the radiation detector 21B are provided. The imaging unit 125A and the imaging unit 125B have different phases in the rotation direction. Therefore, as in the aspect illustrated in FIG. 30, the imaging of the entire circumference around the body axis of the subject S can be completed with a rotation of less than 360°. Therefore, imaging can be completed in a shorter time than that in the first embodiment in which one set of the radiation source 20 and the radiation detector 21 is provided.

In addition, in the second embodiment, as illustrated in FIG. 28, the radiation source elevating mechanism 130 and the detector elevating mechanism 140 are provided as the displacement mechanism for changing the interval between the imaging units 125A and 125B in the rotation axis direction RAD. Therefore, it is possible to smoothly perform the imaging illustrated in FIG. 29 in which the interval between the imaging units 125A and 125B in the rotation axis direction RAD is relatively large and the imaging illustrated in FIG. 30 in which the interval is relatively small with one CT apparatus 10. The burden on the subject S is reduced as compared to a case in which the imaging in which the interval is relatively large and the imaging in which the interval is relatively small are performed by different apparatuses. In addition, it is possible to secure the reproducibility of the positioning of the subject S in the imaging in which the interval is relatively large and the imaging in which the interval is relatively small.

Further, as illustrated in FIG. 29, the imaging control unit 112 images the imaging range CR1 that exceeds the width WA of the detection surface 58 for the radiation R in the radiation detector 21. In this case, the imaging control unit 112 sets the interval between the imaging units 125A and 125B in the rotation axis direction RAD such that the overlapping imaging range OCR occurs between the first projection image 751A and the second projection image 752A and between the first projection image 751B and the second projection image 752B obtained by the imaging units 125A and 125B. As illustrated in FIG. 33, the image processing unit 113 performs the reconstruction process on the ES images generated from the projection images 75 obtained from each of the imaging units 125A and 125B, specifically, the ES image 76A generated from the first projection image 751A and the second projection image 752A and the ES image 76B generated from the first projection image 751B and the second projection image 752B to generate the tomographic images 120A and 120B for the imaging units 125A and 125B, respectively. The image processing unit 113 registers the tomographic images 120A and 120B on the basis of the overlapping imaging range OCR to combine the tomographic images 120A and 120B. Therefore, it is possible to capture the tomographic image 120 covering the imaging range CR1 that exceeds the width WA of the detection surface 58 for the radiation R in the radiation detector 21. In addition, after the ES images 76A and 76B are registered on the basis of the overlapping imaging range OCR and are combined, the reconstruction process may be performed on the combined ES image to generate the tomographic image 120.

Figure 34:
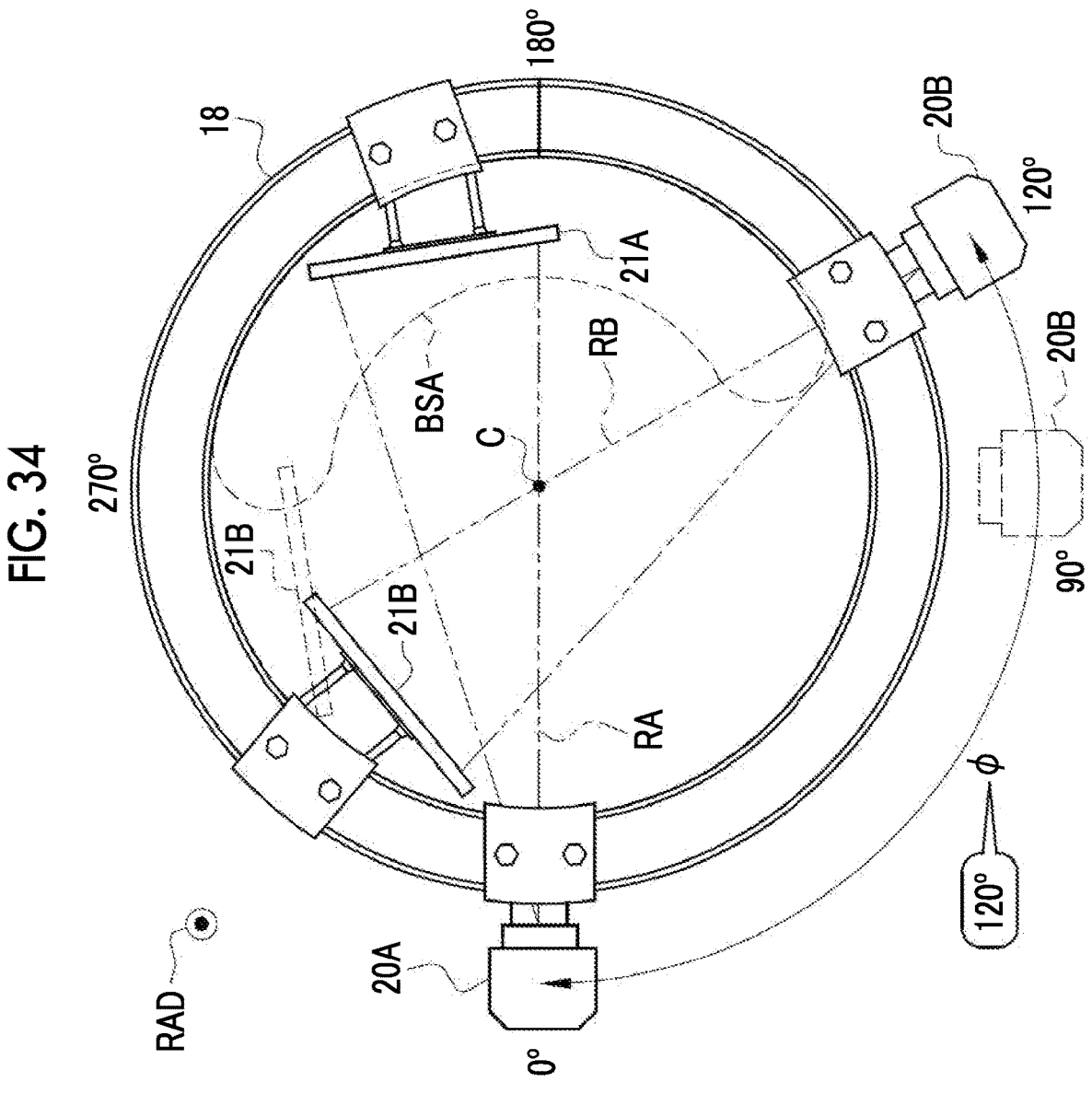
FIG. 34 is a diagram illustrating an example in which the radiation sources are disposed at positions that are separated by 120°.

In addition, the angle φ between the positions where the radiation sources 20A and 20B are disposed is not limited to 90° given as an example. For example, as illustrated in FIG. 34, φ may be set to 120°. Assuming that φ is 120°, the rotation angle of the frame 18 in the aspect illustrated in FIG. 30 can be set to about 240°, and it is possible to complete imaging in a shorter time.

Further, in a case in which φ is set to 120°, the radiation detector 21B can be disposed at a position avoiding a region BSA that is particularly strongly affected by backscattered rays of the radiation RA. Specifically, in a case in which the angle φ is 90°, an end of the radiation detector 21B enters the region BSA as represented by a broken line. Then, in this example, since the radiation RA and the radiation RB are emitted at the same time, components caused by the back-scattered rays of the radiation RA are included as noise in the first projection image 751B and the second projection image 752B obtained by the radiation detector 21B. However, in a case in which φ is set to 120°, it is possible to reduce the concern that the components caused by the backscattered rays of the radiation RA will be included as noise in the first projection image 751B and the second projection image 752B obtained by the radiation detector 21B. The backscattered rays referred to here are scattered rays caused by the disposition of the radiation source 20 and the radiation detector 21. However, since the radiation detector 21B is disposed at the position avoiding the region BSA, it is also possible to reduce the influence of scattered rays caused by the subject S.

In addition, for example, a grid may be provided in front of the radiation detector 21 to reduce the influence of scattered rays. Alternatively, for example, the technique described in JP6006193B that achieves the same image quality improvement effect as that in a case in which a grid is used with image processing, without actually using the grid may be applied.

There is an upper limit to the angle cp. For example, as in a case illustrated in FIG. 35 in which the angle φ is 125°, the end of the radiation detector 21B should not be included in the projection image 75 obtained by the imaging unit 125A. Therefore, it is preferable that the angle φ is greater than 90° and is equal to or less than a limit angle at which the end of the radiation detector 21B is included in the projection image 75 obtained by the imaging unit 125A.

Figure 35:
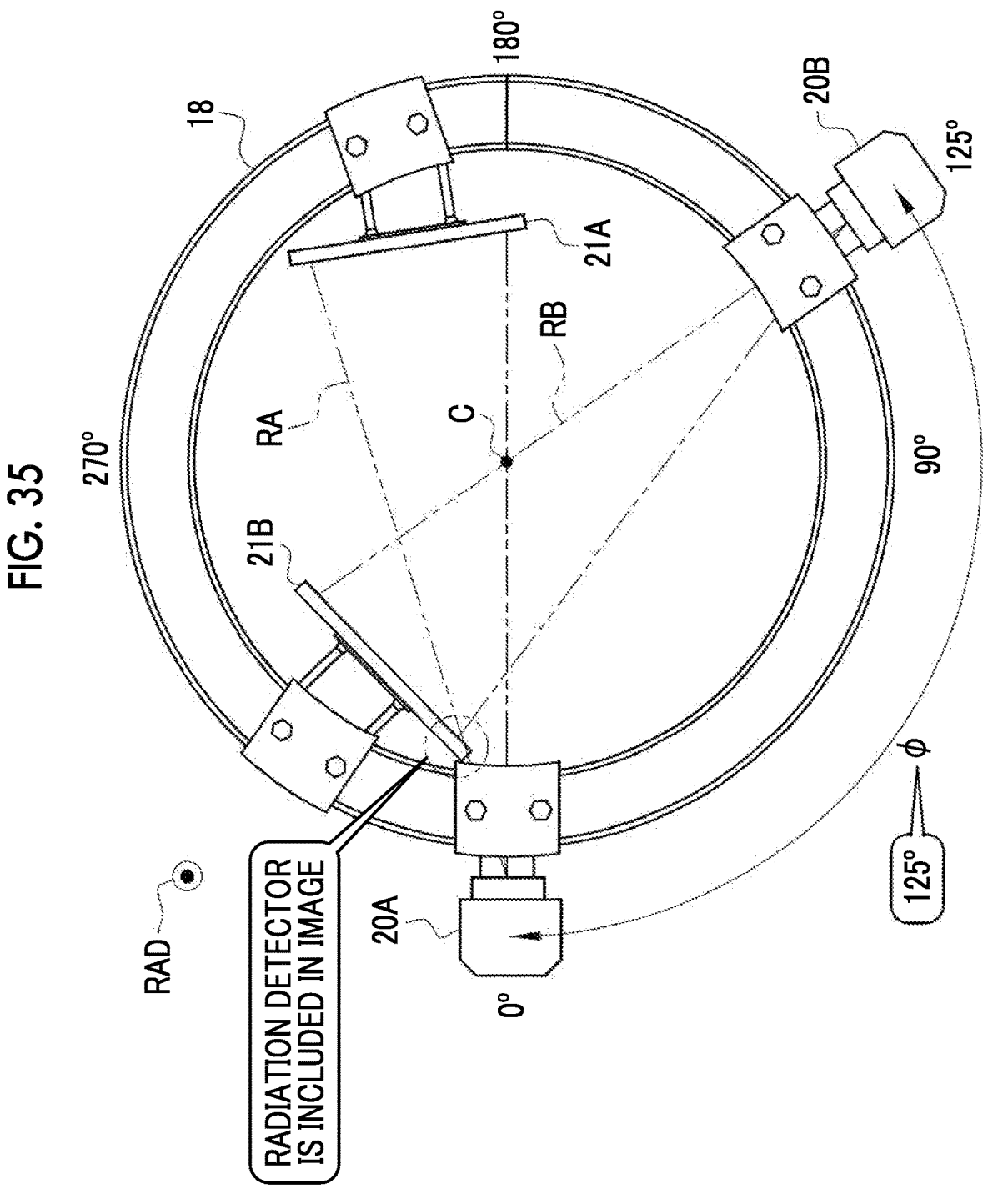
FIG. 35 is a diagram illustrating an example in which the radiation sources are disposed at positions that are separated by 125°.

Further, in a case in which the size of the radiation detector 21 is reduced, the inclusion of the radiation detector 21 in the projection image 75 as illustrated in FIG. 35 is avoided even though the angle φ is increased. However, as the size of the radiation detector 21 is reduced, the scan field of view sFOV is narrowed. Further, in a case in which the rotation radius of the radiation detector 21 (the distance between the rotation center C and the center point CS of the detection surface 58 of the radiation detector 21) increases, it is possible to increase the angle φ. However, since the radiation detector 21 is separated from the subject S, the scan field of view sFOV is also reduced in this case. Therefore, it is preferable that the ratio of the rotation radius of the radiation source 20 (the distance between the rotation center C and the focus of the radiation R of the radiation source 20) to the rotation radius of the radiation detector 21 is set to about 2:1 (for example, the rotation radius of the radiation source 20 is 800 mm, and the rotation radius of the radiation detector 21 is 400 mm) to secure a relatively wide scan field of view sFOV.

Alternatively, in a case in which the size of the frame 18 increases to increase the SID, it is possible to increase the angle φ without separating the radiation detector 21 from the subject S. However, it is necessary to prepare a high-output rotary motor 47 in accordance with the frame 18 that has become larger and heavier, or it is necessary to thicken the column 14 to increase rigidity. In addition, it is necessary to increase the power of the radiation R as the SID is longer. From the above, it is also preferable that the angle φ is about 90° to 120° as in this example.

The imaging unit 125A is fixed at the upper end position. However, the present disclosure is not limited thereto. The radiation source elevating mechanism and the detector elevating mechanism may also be provided in the imaging unit 125A to raise and lower the imaging unit 125A in the rotation axis direction RAD.

The number of imaging units is not limited to two given as an example. For example, three imaging units may be provided at intervals of 120°. In a case in which the number of imaging units increases, it is possible to further reduce the rotation angle in the case of the aspect illustrated in FIG. 30 in which the height positions of the imaging units are aligned with the same position, and it is possible to complete imaging in a shorter time.

Third Embodiment

Figure 36:
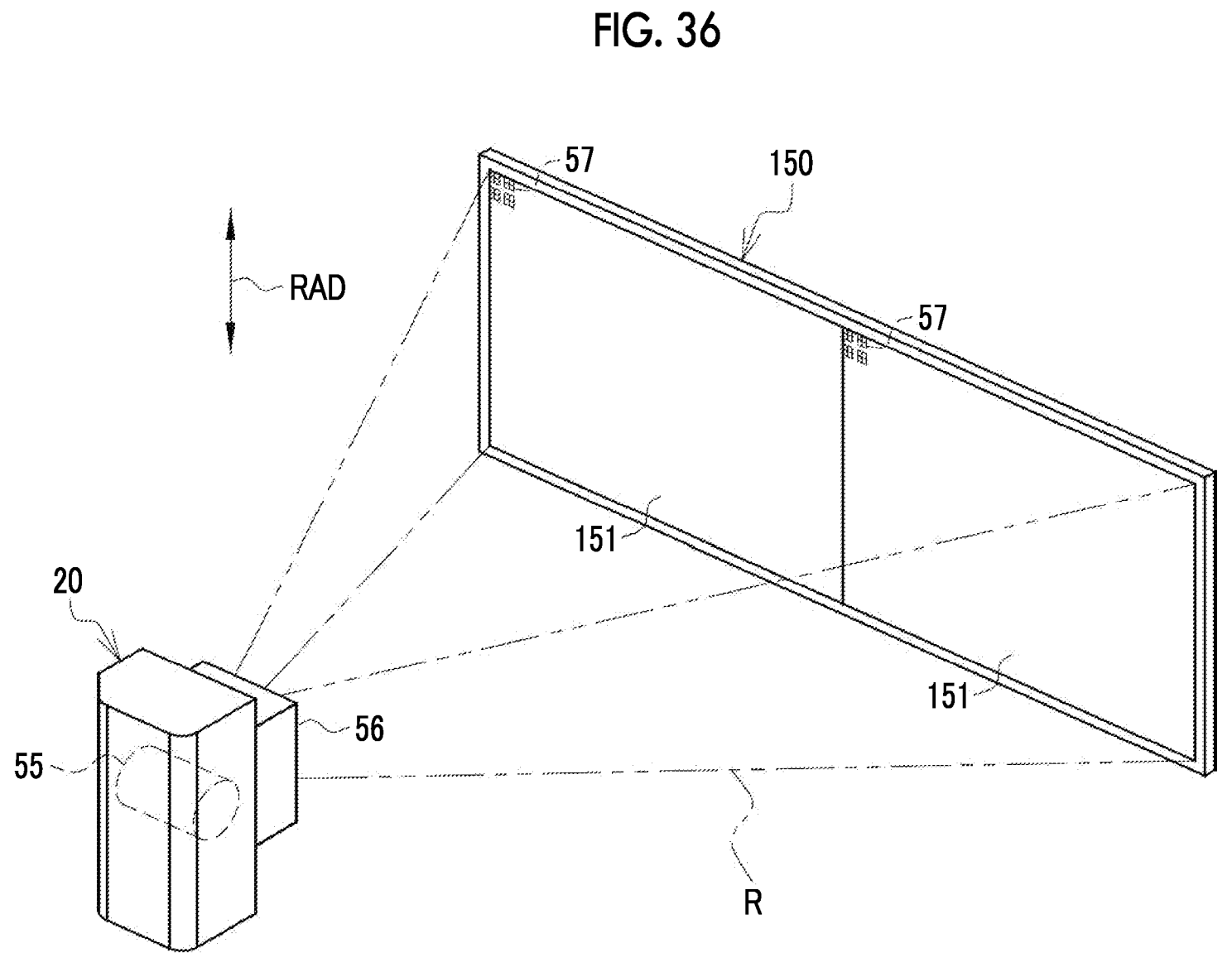

In a third embodiment, for example, a radiation detector 150 illustrated in FIG. 36 is used. The radiation detector 150 has a configuration in which two detection units 151 for the radiation R are arranged along a direction orthogonal to the rotation axis direction RAD. Here, the detection unit 151 is composed of the above-described scintillator and TFT substrate.

In a case in which the radiation detector 150 is used, the radiation detector 150 is disposed at the reference position facing the radiation source 20. Then, the frame 18 is rotated by 180°+θ, the radiation source 20 alternately and continuously emits the first radiation R1 and the second radiation R2 at each preset angle, and the radiation detector 150 outputs the first projection image 751 and the second projection image 752. Alternatively, in order to obtain the tomographic image 120 having higher quality, the frame 18 is rotated by 360°+θ, the radiation source 20 alternately and continuously emits the first radiation R1 and the second radiation R2 at each preset angle, and the radiation detector 150 outputs the first projection image 751 and the second projection image 752. In a case in which the frame 18 is rotated by 180°+θ and it is desired to image a wider range along the rotation axis direction RAD, the height position of the frame 18 is changed. Then, the frame 18 is rotated by 180°+θ in a rotation direction opposite to the rotation direction before the change.

As described above, in the third embodiment, the radiation detector 150 having the configuration in which a plurality of detection units 151 for the radiation R are arranged along the direction orthogonal to the rotation axis direction RAD is used. Therefore, it is possible to image a wider range in the direction orthogonal to the rotation axis direction RAD at one time. In addition, the radiation detector 150 may be disposed at the offset position.

Fourth Embodiment

Figure 37:
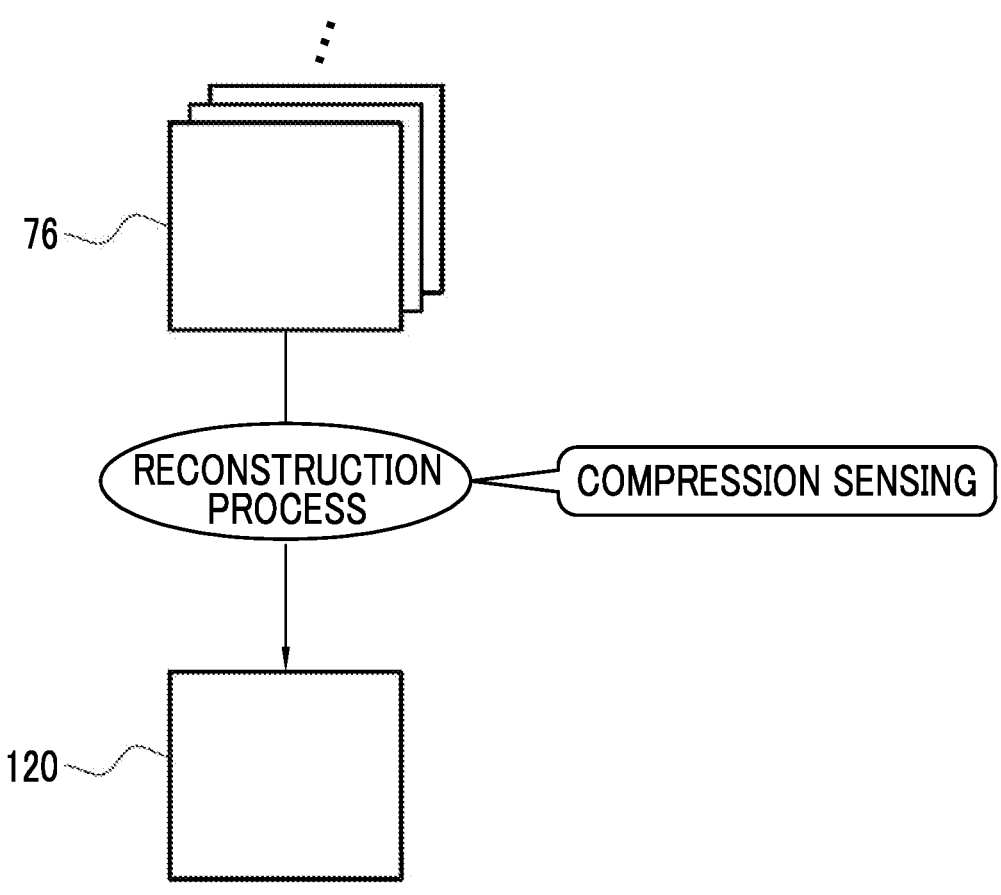
FIG. 37 is a diagram illustrating an aspect in which a compression sensing method is used in a case in which a reconstruction process is performed on projection images to generate a tomographic image.

For example, as illustrated in FIG. 37, in a fourth embodiment, in a case in which the image processing unit 113 performs the reconstruction process on the ES images 76 to generate the tomographic image 120, the image processing unit 113 uses a compression sensing method such as total variation (TV) regularization. The compression sensing is a method that solves an inverse problem of performing high-accuracy signal restoration from measurement data whose amount is insufficient. Here, the measurement data is the projection image 75 and the ES image 76, and the data after signal restoration is the tomographic image 120. In addition, here, the case in which the amount of data is insufficient is a case in which the dose of the radiation R is low and/or a case in which the number of projection images 75 is small.

As described above, in the fourth embodiment, the compression sensing method is used in the reconstruction process. Therefore, the dose of the radiation R can be reduced or the number of projection images 75 can be reduced as compared to a case in which the compression sensing method is not used. Therefore, it is possible to reduce the radiation exposure of the subject S and to complete imaging in a shorter time.

Instead of or in addition to the ES image 76, a virtual monochromatic projection image obtained by virtually reproducing the projection image 75 captured with the radiation R having any energy distribution ED may be generated for each acquisition position, and the tomographic image 120 may be generated from the virtual monochromatic projection image. In addition, instead of or in addition to the ES image 76, a separation image obtained by separating a specific portion, such as a calcification, may be generated for each acquisition position, and the tomographic image 120 may be generated from the separation images.

In a case in which a relatively wide range, such as the whole body, is imaged in the first embodiment or the third embodiment, the frame 18 may be raised and lowered two or more times to perform imaging in two or more steps.

A mechanism that moves the radiation source 20 and the radiation detector 21 along a circumferential direction of the frame 18 may be provided to change the positions where the radiation source 20 and the radiation detector 21 are disposed. This configuration makes it possible to retract the radiation source 20 and the radiation detector 21 that interfere with the guidance of the subject S into the apparatus main body 11 to positions that do not interfere with the guidance.

The number of columns 14 may be four or five. Further, a stepping motor may be used as the rotary motor 47, and the rotation position of the frame 18 may be determined by the number of pulses applied to the rotary motor 47. Furthermore, the frame 18 is not limited to the circular ring and may be a polygonal ring.

The hardware configuration of the computer constituting the control device 12 can be modified in various ways. For example, the control device 12 may be configured by a plurality of computers separated as hardware in order to improve processing capacity and reliability. For example, the functions of the receiving unit 110, the RW control unit 111, and the display control unit 114 and the functions of the imaging control unit 112 and the image processing unit 113 are distributed to two computers. In this case, the two computers constitute the control device 12.

As described above, the hardware configuration of the computer of the control device 12 can be appropriately changed according to required performances, such as processing capacity, safety, and reliability. Further, not only the hardware but also an application program, such as the operation program 105, may be duplicated or may be dispersively stored in a plurality of storages in order to secure safety and reliability.

In each of the above-described embodiments, for example, the following various processors can be used as the hardware structure of processing units performing various processes, such as the receiving unit 110, the RW control unit 111, the imaging control unit 112, the image processing unit 113, and the display control unit 114. The various processors include, for example, the CPU 97 which is a general-purpose processor executing software (operation program 105) to function as various processing units, a programmable logic device (PLD), such as a field programmable gate array (FPGA), which is a processor whose circuit configuration can be changed after manufacture, and/or a dedicated electric circuit, such as an application specific integrated circuit (ASIC), which is a processor having a dedicated circuit configuration designed to perform a specific process.

One processing unit may be configured by one of the various processors or by a combination of two or more processors of the same type or different types (for example, a combination of a plurality of FPGAs and/or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As described above, various processing units are configured by using one or more of the various processors as a hardware structure.

In addition, specifically, an electric circuit (circuitry) obtained by combining circuit elements, such as semiconductor elements, can be used as the hardware structure of the various processors.

It is possible to understand the techniques described in the following supplementary notes from the above description.
Supplementary Note 1
A computed tomography apparatus comprising:
a radiation source that emits radiation having a pyramid shape to a subject positioned in either a standing posture or a sitting posture and that includes a radiation tube having a cold cathode;
a radiation detector in which a plurality of pixels detecting the radiation transmitted through the subject are two-dimensionally arranged and which outputs a projection image of the subject;
a rotation mechanism that rotates the radiation source and the radiation detector around a body axis of the subject; and
a processor that controls operations of the radiation source, the radiation detector, and the rotation mechanism,
wherein the processor directs the radiation source to intermittently and alternately emit first radiation having a first energy distribution and second radiation having a second energy distribution different from the first energy distribution whenever the rotation mechanism rotates the radiation source and the radiation detector by a preset angle, directs the radiation detector to output a first projection image based on the first radiation and a second projection image based on the second radiation which are obtained by the intermittent emission of the first radiation and the second radiation, and generates a tomographic image on the basis of the first projection image and the second projection image.

Supplementary Note 2

The computed tomography apparatus according to Supplementary Note 1, wherein the cold cathode is a field emission type having an electron emission source that emits an electron beam using a field emission phenomenon.

Supplementary Note 3

The computed tomography apparatus according to Supplementary Note 1 or 2, further comprising:

a plurality of imaging units each of which is composed of a set of the radiation source and the radiation detector and which have different phases in a rotation direction.

Supplementary Note 4

The computed tomography apparatus according to Supplementary Note 3, further comprising:

a displacement mechanism that changes an interval between the plurality of imaging units in a rotation axis direction.

Supplementary Note 5

The computed tomography apparatus according to Supplementary Note 4, wherein the processor sets the interval such that an overlapping imaging range occurs between the projection images obtained by the imaging units adjacent to each other in a case in which an imaging range that exceeds a width of a detection surface for the radiation in the radiation detector is imaged, performs a reconstruction process on the projection images obtained from each of the plurality of imaging units to generate a plurality of the tomographic images for each of the plurality of imaging units, and registers the plurality of tomographic images on the basis of the overlapping imaging range to combine the plurality of tomographic images.

Supplementary Note 6

The computed tomography apparatus according to Supplementary Note 1 or 2, wherein the radiation detector has a configuration in which a plurality of detection units for the radiation are arranged along a direction orthogonal to a rotation axis direction of the radiation source and the radiation detector.

Supplementary Note 7

The computed tomography apparatus according to any one of Supplementary Notes 1 to 6, wherein the radiation detector is disposed at an offset position that is separated from a reference position facing the radiation source by a preset angle as viewed from the rotation axis direction of the radiation source and the radiation detector.

Supplementary Note 8

The computed tomography apparatus according to any one of Supplementary Notes 1 to 7, wherein the radiation source and the radiation detector are held in a frame, the subject is positioned in the frame, and the radiation source is disposed outside the frame, and the radiation detector is disposed inside the frame as viewed from the rotation axis direction of the radiation source and the radiation detector.

Supplementary Note 9

The computed tomography apparatus according to any one of Supplementary Notes 1 to 8, wherein the processor uses a compression sensing method in a case in which the reconstruction process is performed on the projection images to generate the tomographic image.

Supplementary Note 10

The computed tomography apparatus according to any one of Supplementary Notes 1 to 9, wherein the width of the detection surface for the radiation in the radiation detector is equal to or greater than 300 mm.

In the technology of the present disclosure, the above-described various embodiments and/or various modification examples may be combined with each other as appropriate. In addition, the present disclosure is not limited to the above-described embodiments, and various configurations can be used without departing from the gist of the present disclosure. Furthermore, the technology of the present disclosure extends to a storage medium that non-temporarily stores a program, in addition to the program.

The above descriptions and illustrations are detailed descriptions of portions related to the technology of the present disclosure and are merely examples of the technology of the present disclosure. For example, the above description of the configurations, functions, operations, and effects is the description of examples of the configurations, functions, operations, and effects of portions related to the technology of the present disclosure. Therefore, unnecessary portions may be deleted or new elements may be added or replaced in the above descriptions and illustrations without departing from the gist of the technology of the present disclosure. In addition, in the above descriptions and illustrations, the description of, for example, common technical knowledge that does not need to be particularly described to enable the implementation of the technology of the present disclosure is omitted in order to avoid confusion and facilitate the understanding of portions related to the technology of the present disclosure.

In the specification, "A and/or B" is synonymous with "at least one of A or B". That is, "A and/or B" means only A, only B, or a combination of A and B. Further, in the specification, the same concept as "A and/or B" is applied to a case in which the connection of three or more matters is expressed by "and/or".

All of the documents, the patent applications, and the technical standards described in the specification are incorporated by reference herein to the same extent as each individual document, each patent application, and each technical standard are specifically and individually stated to be incorporated by reference.

What is claimed is:

1. A computed tomography apparatus comprising:

a radiation source that emits radiation having a pyramid shape to a subject positioned in either a standing posture or a sitting posture and that includes a radiation tube having a cold cathode;

a radiation detector in which a plurality of pixels detecting the radiation transmitted through the subject are two-dimensionally arranged and which outputs a projection image of the subject;

a rotation mechanism that rotates the radiation source and the radiation detector around a body axis of the subject;

a plurality of imaging units each of which is composed of a set of the radiation source and the radiation detector and which have different phases in a rotation direction;

a displacement mechanism that changes an interval between the plurality of imaging units in a rotation axis direction; and a processor that controls operations of the radiation source, the radiation detector, and the rotation mechanism, wherein the processor directs the radiation source to intermittently and alternately emit first radiation having a first energy distribution and second radiation having a second energy distribution different from the first energy distribution whenever the rotation mechanism rotates the radiation source and the radiation detector by a preset angle, directs the radiation detector to output a first projection image based on the first radiation and a second projection image based on the second radiation which are obtained by the intermittent emission of the first radiation and the second radiation, and generates a tomographic image on the basis of the first projection image and the second projection image.

2. The computed tomography apparatus according to claim 1, wherein the cold cathode is a field emission type having an electron emission source that emits an electron beam using a field emission phenomenon.

3. The computed tomography apparatus according to claim 1, wherein the processor sets the interval such that an overlapping imaging range occurs between the projection images obtained by the imaging units adjacent to each other in a case in which an imaging range that exceeds a width of a detection surface for the radiation in the radiation detector is imaged, performs a reconstruction process on the projection images obtained from each of the plurality of imaging units to generate a plurality of the tomographic images for each of the plurality of imaging units, and registers the plurality of tomographic images on the basis of the overlapping imaging range to combine the plurality of tomographic images.

4. The computed tomography apparatus according to claim 1, wherein the radiation detector has a configuration in which a plurality of detection units for the radiation are arranged along a direction orthogonal to a rotation axis direction of the radiation source and the radiation detector.

5. The computed tomography apparatus according to claim 1, wherein the radiation detector is disposed at an offset position that is separated from a reference position facing the radiation source by a preset angle as viewed from a rotation axis direction of the radiation source and the radiation detector.

6. The computed tomography apparatus according to claim 1, wherein the radiation source and the radiation detector are held in a frame, the subject is positioned in the frame, and the radiation source is disposed outside the frame, and the radiation detector is disposed inside the frame as viewed from a rotation axis direction of the radiation source and the radiation detector.

7. The computed tomography apparatus according to claim 1, wherein the processor uses a compression sensing method in a case in which a reconstruction process is performed on the projection images to generate the tomographic image.

8. The computed tomography apparatus according to claim 1, wherein a width of a detection surface for the radiation in the radiation detector is equal to or greater than 300 mm.

* * * * *